United States Patent
Perez

(12) 
(10) Patent No.: US 8,475,807 B2
(45) Date of Patent: Jul. 2, 2013

(54) AVIAN INFLUENZA VIRUS LIVE ATTENUATED VACCINE AND USES THEREOF

(75) Inventor: Daniel R. Perez, Olney, MD (US)

(73) Assignee: University of Maryland College Park, College Park, MD (US)

( * ) Notice: Subject to any disclaimer, the term of this patent is extended or adjusted under 35 U.S.C. 154(b) by 180 days.

(21) Appl. No.: 12/381,550

(22) Filed: Mar. 13, 2009

(65) Prior Publication Data

US 2011/0150912 A1    Jun. 23, 2011

Related U.S. Application Data

(60) Provisional application No. 61/036,213, filed on Mar. 13, 2008.

(51) Int. Cl.
*C12Q 1/70* (2006.01)
*C12N 15/00* (2006.01)

(52) U.S. Cl.
USPC .................. 424/209.1; 435/252.3; 435/235.1; 435/236; 435/325

(58) Field of Classification Search
None
See application file for complete search history.

(56) References Cited

PUBLICATIONS

Song et al. (Journal of Virology, Jun. 27, 2007, vol. 81, p. 9238-9248).*
Jin et al. (Journal of Virology, 2004, vol. 78, p. 995-998).*
Bock et al. (The Journal of Biological Chemistry, 2004, vol. 279, p. 33471-33479).*
Choi et al. (Journal of Virology, 2004, vol. 78, p. 8609-8614).*
Subbarao, E. Kanta et al., A Single Amino Acid in the PB2 Gene of Influenza A Virus Is a Determinnat of Host Range. J. Virology, Apr. 1993, vol. 67, p. 1761-1764.

* cited by examiner

*Primary Examiner* — Agnieszka Boesen
(74) *Attorney, Agent, or Firm* — Pratt & Associates, Inc.; Sana A. Pratt

(57) ABSTRACT

Described in this application are attenuated strains of avian influenza virus containing temperature sensitive mutations in addition to a genetic tag in the PB1 gene. The attenuated viruses are useful as avian and mammalian vaccine for protective immunity against homologous and heterologous lethal challenges with influenza virus. A genetically modified avian influenza virus backbone is described which can be used as a master donor strain for the generation of live attenuated vaccines for epidemic and pandemic influenza.

28 Claims, 1 Drawing Sheet

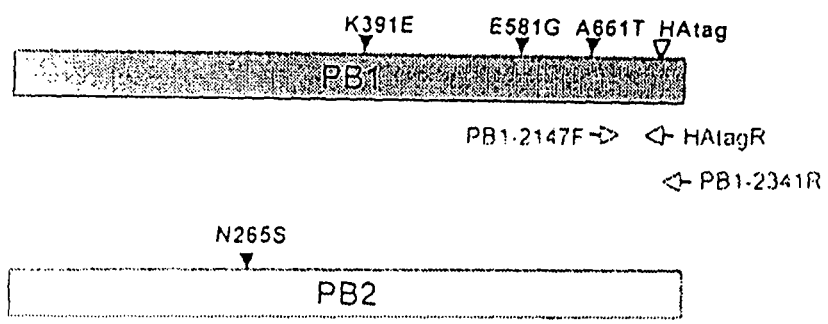

AVIAN INFLUENZA VIRUS LIVE ATTENUATED VACCINE AND USES THEREOF

This application claims the benefit of priority from Provisional Application Ser. No. 61/036,213 filed on Mar. 13, 2008.

STATEMENT OF FEDERALLY SPONSORED RESEARCH AND DEVELOPMENT

This invention was made with government support under NIH Grant No. R01AI05215501A1, R21-AI071014, and U01AI070469-01 awarded by the National Institutes of Health, and CSREES No 2005-35605-15388 and CSREES No 2006-01587 awarded by the United States Department of Agriculture. The US Government has certain rights in the invention.

INTRODUCTION

Globally, influenza is the most economically significant respiratory disease in humans, pigs, horses and poultry (Wright et al., Orthomyxoviruses. In: Fields Virology. Knipe et al., eds. Lippincott Williams & Wilkins, Philadelphia, 2001. pp. 1533-1579.). Influenza virus is known for its continuous genetic and antigenic changes, which impede effective control of the virus (Wright et al. (2001), supra; Webster et al., Microbiol. Rev. 56: 152-179 (1992)). In the 20$^{th}$ century, humans experienced pandemics of influenza with significant death tolls (Horimoto and Kawaoka, 2001, PNAS USA 97, 6108-6113). The emergence of highly pathogenic H5N1 avian influenza virus (AIV) in Asia, with an unusually broad host range and the ability to infect and kill people, has raised concerns that another pandemic is looming over us (Horimoto and Kawaoka, 2001, supra).

Although culling of infected poultry remains the most effective strategy to prevent transmission of avian influenza, when the viruses are widely spread in multiple domestic and wild avian species such as in the case of the Asian H5N1 epidemic, "stamping out" alone is unlikely to be successful. Depopulation of infected flocks in combination with vaccination of at-risk poultry populations is being implemented in several Asian countries, Italy and Mexico as an alternative strategy to control the spread of the disease (Capua and Marangon, 2004, Vaccine 22 4137-4238; Lee et al., 2004, J. Virol. 78, 8372-8381; Marangon and Capua, 2006, Dev. Biol. (Basel) 124, 109-114). Vaccination of high risk birds or flocks has been shown to be an effective complementary tool to control the spread of avian influenza (Ellis et al., 2004, Avian Pathol. 33, 405-412).

There are major limitations in the implementation of vaccination campaigns in Asia due to the endemicity and spread of low and highly pathogenic avian influenza viruses. Inactivated whole avian influenza (AI) virus vaccine and recombinant fowl pox vaccine carrying AI H5 hemagglutinin (HA) require administration of the vaccine to each bird individually by parenteral inoculation; an approach that cannot realistically achieve the mass vaccination that would be required to eradicate the disease. Inactivated vaccines elicit strong humoral responses; however, it is commonly accepted that no adequate mucosal or cellular immunity is achieved (Wareing and Tannock, 2001, Vaccine 19, 3320-3330). Previous exposure to the fowl pox virus would cause inconsistent protection for the birds immunized with the fowl pox vectored vaccine (Swayne et al., 2000, Avian Dis. 44, 132-237). Therefore, the major concern is that the current vaccines may only be effective at lessening disease symptoms, not at preventing virus shedding below transmissible levels. Under these circumstances the vaccine could allow the virus to circulate undetected among birds, further enhancing antigenic drift and spread (Lee et al., 2004, supra; Lipatov et al., 2004, J. Virol. 78, 8951-8959; Savill et al., 2006, Nature 442, 757). This is particularly important in vaccination of domestic ducks, and perhaps other domestic aquatic birds, in which the high efficacy of the vaccine is critical.

Live attenuated vaccines have been shown to protect against diseases in humans and animals while eliminating the risk of infection and/or transmission of the disease. Smallpox and polio in humans and rinderpest in animals are few examples of complete or almost complete eradication of viral diseases using live attenuated vaccines (Fenner et al., 1988. Smallpox and its eradication. World Health Organization, Geneva, Switzerland; Macadam et al., 2006, J. Virol. 80, 8653-8663; Roeder et al., 2004, Dev. Biol. (Basel) 119, 73-91). In poultry, viral diseases are also effectively controlled using modified live vaccines such as Newcastle disease, Gumboro, infectious laringotracheitis, and Marek's disease (Muller et al., 2003, Vet. Microbiol. 97, 153-165; Nair, V. 2004, Dev. Biol. (Basel) 119, 147-154; Veits et al., 2003, J. Gen. Virol. 84, 3343-3352). In ovo administration of live attenuated vaccines to 18-day-old embryo has been widely applied to commercial broilers in USA, mainly against Marek's disease. In addition, automated in ovo vaccination delivers a more uniform dose of vaccine to the embryo and elicits early immunity than manual vaccination of the post-hatching chicks (Ahmad and Sharma, 1993, Avian Dis. 37, 485-491; Sharma and Burmester, 1982, Avain Dis. 26, 134-149).

In the 1960's, Maassab and collaborators developed live attenuated vaccines for type A and B human influenza viruses by serial passage of the wild type virus at successively low temperature in chicken embryo kidney (CEK) cells (Maassab, 1969, J. Immunol. 102, 728-732). Murphy et al. and Subbarao et al. developed alternative approaches for the generation of live attenuated vaccines for humans using reassortants between avian (AI) and human influenza A viruses (Murphy et al., 1997, Vaccine 15, 1372-1378; Murphy et al., 1982, Science 218, 1330-1332; Subbarao et al., 1995, Virus Res. 39, 105-118). The main concept behind these latter approaches was based on the host-range restriction shown by AI viruses. Thus, viruses carrying genes derived from an AI virus would be attenuated in humans, whereas the presence of the human HA and neuraminidase (NA) surface proteins would elicit a protective immune response against circulating influenza A viruses. These experimental vaccines showed great promise in preclinical studies and in clinical studies in adults and older children (Sears et al., 1988, J. Infect. Dis. 158, 1209-1219; Steinhoff et al., 1990, J. Infect. Dis. 162, 394-401). Unfortunately, some of these vaccines caused reactogenicity within young children and infants resulting in high fever and other flu-like symptoms and also the consistent failure to obtain some of the reassortant viruses made these approaches impractical (Steinhoff et al., 1991, J. Infect. Dis. 163, 1023-1028; Steinhoff et al., 1990, supra).

The advent of reverse genetics has opened up new alternatives for the development of live attenuated vaccines (Neumann & Kawaoka, 2001, Virology 287, 243-250). This is particularly important considering the unprecedented emergence of multiple strains of avian influenza viruses with unexpected broad host range (Capua & Marangon, 2004, supra). If one of these strains were spread among a broad range of animal species, we should expect major health, economic and ecological consequences. It is unrealistic to consider the preparation of multiple vaccine formulations specifically tailored for multiple animal species, if such strain were to emerge (Capua & Alexander, 2002; 2004, Avian Pathol. 33, 393-404; Capua & Marangon, 2004, supra).

Recently, a trivalent, live attenuated (att), cold-adapted (ca), temperature sensitive (ts) reassortant vaccine (Flumist®) was licensed for use in humans in the United States (Meadows, M. 2003, FDA Consum. 37, 27). The ca/ts/att influenza A virus contains HA and NA gene segments derived from the currently circulating wild type strain and the PB2, PB1, PA, NP, M and NS gene segments from the ca/ts/att master donor virus (MDV-A), A/Ann Arbor/6/60 (H2N2). The viruses replicate efficiently at 25° C. (ca) but are restricted at 39° C. (ts), and do not replicate in the lungs of infected ferrets (att). The ca/ts/att influenza vaccines are safe, genetically stable, nontransmissible, and likely more immunogenic than inactivated vaccines (King et al., 1998, J. Infect. Dis. 177, 1394-1397; Mendelman et al., 2001, Vaccine 19, 2221-2226). Administered intranasally, live attenuated vaccines provide long lasting protection and induce both systemic and secretory-IgA antibodies, and cell-mediated immunity, which closely resemble the natural infection (Clements et al, 1984, Lancet 1, 705-708; Cox et al., 2004, J. Immunol. 59, 1-15).

Live attenuated avian influenza vaccines for poultry have not yet been developed. There is a need for a live attenuated avian influenza vaccine that can be administered economically to multiple domestic poultry species, and that can also serve as a vaccine donor for influenza viruses of other animal species.

SUMMARY OF THE INVENTION

In this application is described a genetically modified reasserted avian influenza virus (AIV) which induces protective immunity against highly lethal influenza strains in poultry and in mice. The modified AIV backbone of the present invention can be used as a donor for influenza vaccines for avian and mammalian species.

The inventors used the influenza virus backbone influenza A/Guinea fowl/Hong Kong/WF10/99 (H9N2) (WF10), for its potential as a suitable virus vaccine donor that could be used in multiple animal species, including humans. H9N2 viruses of the same lineage as the WF10 virus have been shown to effectively infect multiple domestic poultry species, including ducks, turkeys, chickens and quail as well as mice without prior adaptation (Choi et al., 2004, J. Virol. 78, 8609-8614; Guan et al., 2000, J. Virol. 74, 9372-9380; Lin et al., 2000, PNAS USA 97, 9654-9658; Peiris et al., 2001, J. Virol. 75, 9679-9686; Peiris et al., 1999, Lancet 354, 916-917; Perez et al., 2003a, J. Virol. 77, 3148-3156; Perez et al., 2003b, Avian Dis. 47, 1114-1117; Xu et al., 2004, Microbes Infect. 6, 919-925). Viruses phylogenetically related to the WF10 virus were also isolated from pigs (Xu et al., 2004, supra). Furthermore, the inventors have shown that the WF10 virus shares many biological features similar to human influenza viruses, including their ability to infect nonciliated cells in cultures of human airway epithelial cells (Wan and Perez, 2007, J. Virol. 81, 5181-5191). Thus, WF10 represents an ideal candidate for the preparation of live vaccines applicable to multiple animal species.

Analysis of the attenuated A/Ann Arbor/6/60 (H2N2), the master donor of the ca human influenza virus, revealed 11 amino acid mutations compared to the wild type virus (Cox et al., 1988, Virology 167, 554-567). Among these mutations, only five ts loci, three in the PB1 gene (K391E, E581G, A661T), one in the PB2 gene (N265S), and one in the NP gene (D34G), were sufficient to confer to the influenza A/Puerto Rico/8/34 (H1N1) virus the ts phenotype in vitro and the att phenotype in ferrets (Jin et al., 2004, J. Virol. 78, 995-998). Sequence alignment of the PB1 and PB2 genes revealed that avian influenza viruses do not carry the amino acid mutations found in the ca/ts A/Ann Arbor/6/60 strain.

Using these same ts mutations in PB1 and PB2 of WF10 conferred the ts phenotype in vitro to WF10. The mutation in the NP gene was already in the WF10 strain. Even though the resulting mutant WF10 was found to be ts, the mutant virus was not attenuated in chickens. Thus, additional modifications in the genomes of the avian influenza viruses were necessary in order to produce a live att avian influenza virus.

For this purpose, a genetic tag was engineered in fusion with the C terminal of virus PB1 protein and the mutant virus harboring both the ca/ts mutations and the genetic tag was rescued, a double-mutant. The double-mutant strain with the genetic tag could be easily discriminated from the field isolates by real-time PCR using specific primers. The viruses harboring either the genetic tag or the ts muations were not as attenuated in cell cultures at higher temperature as the double-mutant att virus, suggesting that the genetic tag and the ts mutations worked synergistically to contribute to the ts effect. Most importantly, the genetic tag was essential for the attenuated phenotype of the virus, att WF10, both in vitro and in vivo.

Using the att WF10 as a backbone, we substituted the HA and NA from different pathogenic viruses, low pathogenic avian influenza virus (LPAI) H7N2 and highly pathogenic influenza virus (HPAI) H5N1 for vaccine purposes in order to determine whether this backbone would work as a vaccine candidate. In chickens, a vaccination scheme consisting of a single dose of an att H7N2 vaccine virus at 2 weeks of age and subsequent challenge with the wild type H7N2 resulted in complete protection. A single dose immunization in ovo with the att H5N1 vaccine virus in 18-day old chicken embryos resulted in more than 60% protection for 4 week-old chickens and 100% protection for 9 to 12 week-old chickens. Boosting at 2 weeks post-hatching, provided 100% protection against challenge with the HPAI H5N1 virus for chickens as young as 4-weeks old, with undetectable virus shedding post-challenge.

To characterize further the biological properties of attenuated viruses using the att WF10 backbone, additional recombinant viruses were created and tested. These recombinants carry the internal genes of the genetically modified WF10 and the HA and NA of the highly lethal influenza A/WSN/33 (H1N1) virus and A/Vietnam/1203/04 (H5N1). The 6WF10att:2H1N1 carrying both the ca/ts loci and the genetic tag was found to be attenuated in mice, i.e. the virus replicated poorly in mouse lungs. Even in the context of HPAI H5N1 surface genes, the 6WF10att:2H5N1 mutant was noticeably less virulent than wild type virus, indicating that the WF10att backbone is attenuated in mice, whichever surface proteins are present. Mice immunized with 6WF10att:2H1N1 virus survived challenge with the wild type WSN virus. Immunization with the recombinant attenuated H5N1 also protected mice from lethal challenge with HPAI H5N1.

Furthermore, WF10att backbone provided protection in mice against heterologous challenge. Mice immunized with a heterologous subtype 6WF10att:2H7N2 virus survived challenge with both WSN virus and HPAI H5N1. Similar results were achieved when mice were immunized with another WF10att subtype virus, the 6WF10att:2H9N2 virus, suggesting that protection by the WF10att backbone is cell-mediated.

These studies highlight the potential of this genetically modified avian influenza virus backbone as the donor for influenza vaccines for avian and mammalian species.

Therefore, in one aspect, the present invention provides a modified reassortant avian influenza virus which is cold-adapted, temperature-sensitive, and attenuated. The avian influenza virus has an att phenotype in birds, i.e. a virus with only limited replication in the upper respiratory tract of birds, unable to cause disease, unable to transmit and shed in feces, and able to protect against field infections. The modified attenuated virus is useful as a live attenuated vaccine against avian influenza.

In one embodiment of the invention, the attenuated reassortant influenza virus is produced by introducing cold-adapted/temperature sensitive mutations, hereafter, ts loci, in the PB1 (K391E, E457D, E581G, A7661T) and PB2 (N265S) genes of an avian influenza strain, and cloning a genetic tag in the PB1 gene. These mutations provide attenuation, however, the combination of any of these mutations with the genetic tag in PB1 and possibly genetic tags in other parts of the genome can provide a similar attenuated phenotype. In the Examples below, the inventors have shown that similar attenuation phenotypes can be achieved with one, two, three, or four ts mutations in the context of the genetic tag. The mutations can be introduced into the viral genome by any method known in the art, for example by site-directed mutagenesis.

The genetic tag can be the specific sequence defined in SEQ ID NO:1, or any other random sequence. One or more genetic tag can be inserted either in frame or out of frame, in any of the influenza genes as long as viral replication is maintained. The genetic tag can be of any size as long as it does not destroy virus viability. The genetic tag described in the Examples was cloned in frame in PB1 using convenient restriction sites. It is believed that the tag at the C-terminus of PB1 affects its folding at the restrictive temperature and thus its replicase activity is affected. Other similar genomic locations which potentially affect the function of other influenza proteins could be used to provide an attenuated phenotype by itself or in the context of other ts mutations. In an exemplary embodiment, the genetic tag is 8 amino acids derived from the influenza virus H3 HA protein sequence and corresponding to YPYDVPDY (SEQ ID NO:1), hereafter the HA tag. The HA tag can be incorporated in the context of wild-type and ts PB1 sequences such that the C terminus of the PB1 gene at the HA tag junction contains the following sequence: E DMYPYDVPDYASRICSTIEELRRQK-C terminus (SEQ ID NO:2), in which the underlined amino acids correspond to artificially introduced amino acids, those in italics correspond to the HA tag, and the rest to PB1.

In another embodiment, the attenuated avian influenza virus is A/Guinea Fowl/Hong Kong/WF 10/99 (H9N2) containing ts mutations and a genetic tag. In an exemplary embodiment, the ts mutations are K391E, E581G and A661T in PB1, and N265S in PB2, and the genetic tag is HA protein sequence corresponding to YPYDVPDY (SEQ ID NO:1) and incorporated in frame with the C terminus of PB1 open reading frame while preserving the essential assembly sequences. In yet another embodiment, cold-adapted/temperature-sensitive attenuated A/Guinea Fowl/Hong Kong/WF 10/99 (H9N2) is 7attWF10 having a PB1 sequence identified in SEQ ID NO:3, useful as a vaccine for birds, including ducks, turkeys, chickens and quail and as a donor backbone for producing live attenuated vaccines for use in birds and mammals.

In yet another embodiment, the attenuated virus is A/Mallard/Alberta/01 (H7N3) containing ts mutations and a genetic tag. In an exemplary embodiment, the ts mutations are K391E, E581G and A661T in PB1, and N265S in PB2, and the genetic tag is HA protein sequence corresponding to YPYDVPDY (SEQ ID NO:1) and incorporated in frame with the C terminus of PB1 open reading frame while preserving the essential assembly sequences. In yet another embodiment, cold-adapted/temperature-sensitive attenuated A/Mallard/Alberta/01 is 7attWF10:1malH7, which contains the HA and NA genes of the A/Mallard/Alberta/01 (H7N3) and the internal genes corresponding to the WF10 att backbone containing the ts mutations and HA tag, with a PB1 gene sequence identified in SEQ ID NO:3. This virus strain replicates restrictively in aquatic birds and is useful as a vaccine for aquatic birds, or as a donor backbone for producing live attenuated vaccines for use in aquatic birds.

In another embodiment, the attenuated avian influenza virus is A/Chicken/Delaware/VIVA/04 (H7N2) (Ck/04) containing ts mutations and a genetic tag. In an exemplary embodiment, the ts mutations are K391E, E581G and A661T in PB1, and N265S in PB2, and the genetic tag is HA peptide sequence corresponding to YPYDVPDY (SEQ ID NO:1) and incorporated in frame with the C terminus of PB1 open reading frame while preserving the essential assembly sequences. In yet another embodiment, cold-adapted/temperature-sensitive attenuated Ck/04 is 6attWF10:2ckH7N2 containing surface genes of Ck/04 (H7N2) and internal genes of the att WF10 having ts mutations and a genetic tag, with a PB1 sequence identified in SEQ ID NO:3. The attenuated virus is useful as a vaccine for chickens, and as a donor backbone for producing live attenuated vaccines for use in birds.

In yet another embodiment, the attenuated avian influenza virus is A/Vietnam/1203/04 or A/VN/1203/04 (H5N1) containing ts mutations and a genetic tag. In an exemplary embodiment, the ts mutations are K391E, E581G and A661T in PB1, and N265S in PB2, and the genetic tag is HA protein sequence corresponding to YPYDVPDY (SEQ ID NO:1) and incorporated in frame with the C terminus of PB1 open reading frame while preserving the essential assembly sequences. In yet another embodiment, cold-adapted/temperature-sensitive attenuated 6attWF10:2 H5N1 which contains the HA and NA genes of A/VN/1203/04 (H5N1) virus, and internal genes of the att WF10 having ts mutations and a genetic tag, with a PB1 gene sequence identified in SEQ ID NO:3. In still another embodiment, cold-adapted/temperature-sensitive attenuated 6attWF10:2ΔH5N1 which contains the HA and NA genes of A/VN/1203/04 (H5N1) further having the multiple basic amino acids of the HA cleavage site removed as found in strain 6PR8:2ΔH5N1 (as provided by Centers for Disease Control), and the internal genes corresponds to the WF10 att backbone containing the ts mutations and HA tag, said PB1 gene of said 6attWF10:2ΔH5N1 identified in SEQ ID NO:3, useful as a vaccine for chickens, and as a donor backbone for producing live attenuated vaccines for use in birds.

In another embodiment, the attenuated avian influenza virus is A/WSN/33 (H1N1) containing ts mutations and a genetic tag. In an exemplary embodiment, the ts mutations are K391E, E581G and A661T in PB1, and N265S in PB2, and the genetic tag is HA protein sequence corresponding to YPYDVPDY (SEQ ID NO:1) and incorporated in frame with the C terminus of PB1 open reading frame while preserving the essential assembly sequences. In yet another embodiment, cold-adapted/temperature-sensitive attenuated 6WF10att:2H1N1 which contains the HA and NA genes of the virus A/WSN/33 (H1N1) and the internal genes corresponds to the WF10 att backbone containing the ts mutations and HA tag, with a PB1 gene identified in SEQ ID NO:3, useful as a vaccine for birds and mammals, and as a donor backbone for producing live attenuated vaccines for use in birds and mammals.

In yet another embodiment, a modified PB1 sequence is provided wherein the PB1 contains temperature sensitive mutations in PB1 (K391E, E457D, E581G, A7661T) and an HA tag. In an exemplary embodiment the modified PB1 is from A/Guinea Fowl/Hong Kong/WF 10/99 (H9N2) avian influenza virus. The WF10 modified PB1 carrying the ts mutations and the HA tag is specified in SEQ ID NO:3 and a peptide sequence identified in SEQ ID NO; 4. The modified PB1 sequence can be provided on a vector for use in creating reassortant influenza virus.

In still another embodiment, a modified PB1 sequence is provided wherein the PB1 contains a genetic tag. In an exemplary embodiment, the genetic tag is an HA tag having peptide sequence corresponding to YPYDVPDY (SEQ ID NO:1) and incorporated in frame with the C terminus of PB1 open reading frame while preserving the essential assembly sequences. The genetic tag can be used to differentiate field isolates from recombinant virus strains containing the HA tag, or for example to differentiate between birds vaccinated with a recombinant virus vaccine versus the naturally infected birds. The HA tag can be detected using PCR primers specific for the HA tag, such as HAtag R primer identified in SEQ ID NO:5, PB1-2147F identified in SEQ ID NO:6, and PB1-2431R identified in SEQ ID NO:7.

In another embodiment, a method for producing live attenuated avian influenza virus is provided, the method comprising (a) introducing at least one mutation at the following amino acid positions of the avian influenza virus PB1 (K391E, E457D, E581G, A7661T) and PB2 (N265S), (b) introducing a genetic tag in fusion with PB1 genes of the avian influenza virus; (c) replicating the modified influenza virus genome under conditions whereby virus is produced; and (d) isolating live attenuated avian influenza virus. In an exemplary embodiment, the genetic tag is an HA tag having peptide sequence corresponding to YPYDVPDY (SEQ ID NO:1) and incorporated in frame with the C terminus of PB1 open reading frame while preserving the essential assembly sequences.

The invention provides a master donor avian influenza virus strain. The strain is cold-adapted, temperature-sensitive, and attenuated. The strain, WF10att, contains the six internal genes of WF10 virus which has a broad host range. When reassorted with one or two surface genes of a selected circulating influenza virus, the reassortant virus could be used as live-attenuated vaccine to protect against the spread of the circulating virus in different animals and birds. Therefore, in another embodiment, the present invention provides a method for producing a live attenuated influenza virus from a selected influenza virus comprising creating a recombinant virus comprising (a) HA and NA genes of the selected virus, and (b) internal genes corresponding to the WF10att backbone of the invention having ts mutations and a genetic tag.

In still another embodiment, the present invention provides a live attenuated avian virus vaccine comprising recombinant virus comprising internal genes of the att WF10 having ts mutations and a genetic tag of the present invention, in an amount effective to elicit an immune response in a bird or mammal against said recombinant virus; and a pharmaceutically acceptable diluent, carrier, or excipient.

In another embodiment, the present invention provides a method for eliciting in a subject an immune response against a selected influenza virus, the method comprising administering to a subject an amount effective for eliciting an immune response in the subject of a composition comprising a recombinant influenza virus comprising (a) HA and NA genes of the selected virus, and (b) internal genes corresponding to the WF10 att backbone having the ts mutations and HA tag.

Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

BRIEF DESCRIPTION OF THE DRAWINGS

FIG. 1. Schematic representation of avian influenza PB1 and PB2 constructs for the generation of ts and HA tagged mutant viruses. Site-directed mutagenesis was used to introduce three ts mutations (K391E, E581G, A661T) in the PB1 gene and one (N265S) in the PB2 gene of the WF10 (H9N2) virus. The PB1 gene was further modified by incorporating a HA tag sequence in frame with the C-terminus of the PB1 protein. The HAtagR (SEQ ID NO:5) primer is unique for the HA tag sequences (tag), whereas the PB1-2147F (SEQ ID NO:6) and PB1-2341R (SEQ ID NO:7) anneal to sequences in PB1 gene.

DETAILED DESCRIPTION

In order to provide a clearer and consistent understanding of the specification and claims, including scientific and technical terms, the following definitions are provided.

The terms "nucleic acid," "polynucleotide," "polynucleotide sequence" and "nucleic acid sequence" refer to single-stranded or double-stranded deoxyribonucleotide or ribonucleotide polymers, or chimeras or analogues thereof. As used herein, the term optionally includes polymers or analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention encompasses complementary sequences, in addition to the sequence explicitly indicated.

The term "gene" is used broadly to refer to any nucleic acid associated with a biological function. Thus, genes include coding sequences and/or the regulatory sequences required for their expression. The term "gene" applies to a specific genomic sequence, as well as to a cDNA or an mRNA encoded by that genomic sequence.

Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "Tissue specific" promoter or enhancer is one which regulates transcription in a specific tissue type or cell type, or types.

The term "vector" refers to the means by which a nucleic can be propagated and/or transferred between organisms, cells, or cellular components. Vectors include plasmids, viruses, bacteriophage, pro-viruses, phagemids, transposons, and artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not autonomously replicating. Most commonly, the vectors of the present invention are plasmids.

An "expression vector" is a vector, such as a plasmid, which is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer.

A "bi-directional expression vector" is typically characterized by two alternative promoters oriented in the opposite direction relative to a nucleic acid situated between the two promoters, such that expression can be initiated in both orientations resulting in, e.g., transcription of both plus (+) or sense strand, and negative (−) or antisense strand RNAs. Alternatively, the bi-directional expression vector can be an ambience vector, in which the viral mRNA and viral genomic RNA (as a cRNA) are expressed from the same strand.

In the context of the invention, the term "isolated" refers to a biological material, such as a nucleic acid or a protein, which is substantially free from components that normally accompany or interact with it in its naturally occurring environment. The isolated material optionally comprises material not found with the material in its natural environment, e.g., a cell. For example, if the material is in its natural environment, such as a cell, the material has been placed at a location in the cell (e.g., genome or genetic element) not native to a material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids.

The term "recombinant" indicates that the material (e.g., a nucleic acid or protein) has been artificially or synthetically (non-naturally) altered by human intervention. The alteration can be performed on the material within, or removed from, its natural environment or state. Specifically, when referring to a virus, e.g., an influenza virus, the virus is recombinant when it is produced by the expression of a recombinant nucleic acid.

The term "reassortant," when referring to a virus, indicates that the virus includes genetic and/or polypeptide components derived from more than one parental viral strain or source. For example, a 7:1 reassortant includes 7 viral genomic segments (or gene segments) derived from a first parental virus, and a single complementary viral genomic segment, e.g., encoding hemagglutinin or neuramimidase, from a second parental virus. A 6:2 reassortant includes 6 genomic segments, most commonly the 6 internal genes from a first parental virus, and two complementary segments, e.g., hemagglutinin and neuramimidase, from a different parental virus.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation" and "transduction." In the context of the invention a variety of methods can be employed to introduce nucleic acids into prokaryotic cells, including electroporation, calcium phosphate precipitation, lipid mediated transfection (lipofection), etc.

The term "host cell" means a cell which contains a heterologous nucleic acid, such as a vector, and supports the replication and/or expression of the nucleic acid, and optionally production of one or more encoded products including a polypeptide and/or a virus. Host cells can be prokaryotic cells such as E. coli, or eukaryotic cells such as yeast, insect, amphibian, avian or mammalian cells, including human cells. Exemplary host cells in the context of the invention include Vero (African green monkey kidney) cells, human embryonic retinal cells, BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), CEK cells (chicken embryo kidney) and COS cells (e.g., COS1, COS7 cells). The term host cell encompasses combinations or mixtures of cells including, e.g., mixed cultures of different cell types or cell lines (e.g., Vero and CEK cells).

The terms "temperature sensitive," "cold adapted" and "attenuated" for avian influenza viruses are well known in the art. For example, the term "temperature sensitive" ("ts") indicates that the virus exhibits a 100 fold or greater reduction in titer at 39° C.-41° C. relative to 33-35° C. for influenza A strains. For example, the term "cold adapted" ("ca") indicates that the virus exhibits growth at 32-39° C. within 100 fold of its growth at 37-39° C. For example, the term "attenuated" ("att") indicates that the virus replicates in the upper airways of ferrets but is not detectable in lung tissues, and does not cause influenza-like illness in the bird or animal. The attenuated viruses of the present invention carrying the att WF10 backbone show no detectable replication in the lung tissues of birds or mammals and/or no transmission among birds or mammals. It will be understood that viruses with intermediate phenotypes, i.e., viruses exhibiting titer reductions less than 100 fold at 39° C., exhibiting growth at 25° C. that is more than 100 fold than its growth at 33° C. (e.g., within 200 fold, 500 fold, 1000 fold, 10,000 fold less), and/or exhibit reduced growth in the lungs relative to growth in the upper airways of ferrets (i.e., partially attenuated) and/or reduced influenza like illness in the bird or animal, which possess one or more of the amino acid substitutions and a genetic tag described herein are also useful viruses encompassed by the invention. Growth indicates viral quantity as indicated by titer, plaque size or morphology, particle density or other measures known to those of skill in the art.

The expression "artificially engineered" is used herein to indicate that the virus, viral nucleic acid or virally encoded product, e.g., a polypeptide, a vaccine, comprises at least one mutation introduced by recombinant methods, e.g., site directed mutagenesis, PCR mutagenesis, etc. The expression "artificially engineered" when referring to a virus (or viral component or product) comprising one or more nucleotide mutations and/or amino acid substitutions indicates that the viral genome or genome segment encoding the virus (or viral component or product) is not derived from naturally occurring sources, such as a naturally occurring or previously existing laboratory strain of virus produced by non-recombinant methods (such as progressive passage at 25° C.), e.g., a wild type or cold adapted A/Guinea fowl/Hong Kong/WF10 99 strain.

The term "subject" is used herein to refer to any subject which is susceptible to influenza virus infection. The subject can be avian, e.g. chicken, turkeys, ducks and other birds, or mammalian, e.g. swine, horses, dogs, humans and other animals.

Influenza Virus

Influenza virus is an RNA virus belonging to the family Orthomyxoviridae. There are three types of influenza virus A, B and C. Influenza type A viruses are divided into subtypes and named on the basis of two surface proteins, hemaglutinin (HA) and neuraminidase (NA). There are 16 known HA (H1-H16) subtypes and 9 (N-1-N9) known NA subtypes which can combine to form different subtypes, e.g. H1N1, H5N1, etc. Some subtypes are found among animal species, such as H7N7 in horses, and H3N8 in dogs. Only influenza A viruses infect birds, and all known subtypes of influenza A viruses can infect birds. Influenza B and C viruses, usually found only in humans, are not classified according to subtype.

The genome of influenza viruses is composed of eight segments of linear (−) strand ribonucleic acid (RNA), encoding the immunogenic hemagglutinin (HA) and neuramimidase (NA) proteins, and six internal core polypeptides: the nucleocapsid nucleoprotein (NP); matrix proteins (M); non-structural proteins (NS); and 3 RNA polymerase (PA, PB1, PB2) proteins. During replication, the genomic viral RNA is transcribed into (+) strand messenger RNA and (−) strand genomic cRNA in the nucleus of the host cell. Each of the eight genomic segments is packaged into ribonucleoprotein complexes that contain, in addition to the RNA, NP and a polymerase complex (PB1, PB2, and PA).

The viral RNA consists of eight independent segments, which easily recombine among influenza viruses to produce new subtypes.

Nucleoprotein (NP), which is the primary component of the nucleocapsid, is encoded in the fifth segment. The NP and the matrix protein are used to classify the influenza virus into group A, B or C. Since NP is an internal protein, it is not subject to the pressure of selection by a host's immune system. It binds RNA, is part of the transcriptase complex, and is involved in the nuclear-cytoplasmic transport of viral RNA (vRNA).

Neuraminidase (NM), which splits the oc-keto bond that joins a terminal sialic acid and the next sugar residue, thereby allowing the release of viral progeny from infected cells, is encoded by the sixth segment. Nine subtypes (N-1-N9) of this enzyme have been identified. All subtypes have two structural regions—a stalk and a head. All N8 proteins have 470 amino acids, the first eight of which are highly conserved. The following region is rich in hydrophobic amino acids and is considered to be the transmembrane domain. The next 51 amino acids make up the stalk region, and the head region begins at Cys91. The last region contains the catalytic site of the enzyme. Cysteine residues in the head and stalk region tend to be highly conserved. There are 6-8 putative N-glycosylation sites.

Hemagglutinin (HA), which is a membrane glycoprotein responsible for the adsorption of the virus into the host cell, is the main antigen to which neutralizing antibodies are directed. Its antigenic variation is the major cause of influenza epidemics. It is encoded by the fourth segment. Sixteen different subtypes (H1-H16) have been identified. HA has a signal peptide of 16 amino acids and two polypeptides (HA1 and HA2) joined by disulfide bridges. HA1 has the amino terminal end, whereas HA2 has the carboxyl terminal end. A hydrophobic region in HA2 anchors HA to the viral membrane. Cysteine residues tend to be highly conserved. There are six putative glycosylation sites, which enable the virus to mask its antigenic sites (Skehel et al., PNAS USA 81: 1779 (1984)).

Other proteins include matrix (M or M1 and M2), non-structural (NS or NS1 and NS2), PA, PB1, and PB2. The M1 protein is a major component of the virion that binds to the plasma membrane of infected cells by means of two hydrophobic regions at the N-terminus of the protein, whereas M2 is an ion channel and, therefore, an integral membrane protein. The NS1 protein is found in the nucleus and affects cellular RNA transport, splicing, and translation. The NS2 protein is found in the nucleus and cytoplasm and has unknown function. The PA protein is a transcriptase and may have protease activity, whereas the PB1 protein functions in transcription elongation and the PB2 protein functions in transcription cap binding.

In the present invention, viral genomic RNA corresponding to each of the eight segments is inserted into a recombinant vector for manipulation and production of influenza viruses. A variety of vectors, including viral vectors, plasmids, cosmids, phage, and artificial chromosomes, can be employed in the context of the invention. Typically, for ease of manipulation, the viral genomic segments are inserted into a plasmid vector, providing one or more origins of replication functional in bacterial and eukaryotic cells, and, optionally, a marker convenient for screening or selecting cells incorporating the plasmid sequence. An exemplary vector, plasmid is described the examples.

Most commonly, the plasmid vectors of the invention are bi-directional expression vectors capable of initiating transcription of the inserted viral genomic segment in either direction, that is, giving rise to both (+) strand and (−) strand viral RNA molecules. To effect bi-directional transcription, each of the viral genomic segments is inserted into a vector having at least two independent promoters, such that copies of viral genomic RNA are transcribed by a first RNA polymerase promoter (e.g., Pol I), from one strand, and viral mRNAs are synthesized from a second RNA polymerase promoter (e.g., Pol II). Accordingly, the two promoters are arranged in opposite orientations flanking at least one cloning site (i.e., a restriction enzyme recognition sequence) preferably a unique cloning site, suitable for insertion of viral genomic RNA segments. Alternatively, an "ambisense" vector can be employed in which the (+) strand mRNA and the (−) strand viral RNA (as a cRNA) are transcribed from the same strand of the vector.

Expression Vectors

The influenza virus genome segment to be expressed is operably linked to an appropriate transcription control sequence (promoter) to direct mRNA synthesis. A variety of promoters are suitable for use in expression vectors for regulating transcription of influenza virus genome segments. In certain embodiments, CMV RNA Pol II promoter and Human RNA Pol I promoters can be used. If desired, e.g., for regulating conditional expression, other promoters can be substituted which induce RNA transcription under the specified conditions, or in the specified tissues or cells. Numerous viral and mammalian, e.g., human promoters are available, or can be isolated according to the specific application contemplated. For example, alternative promoters obtained from the genomes of animal and human viruses include such promoters as the adenovirus (such as Adenovirus 2), papilloma virus, hepatitis-B virus, polyoma virus, and Simian Virus 40 (SV40), and various retroviral promoters. Mammalian promoters include, among many others, the actin promoter, immunoglobulin promoters, heat-shock promoters, and the like. In addition, bacteriophage promoters can be employed in conjunction with the cognate RNA polymerase, e.g., the T7 promoter.

Transcription is optionally increased by including an enhancer sequence. Enhancers are typically short, e.g., 10-500 bp, cis-acting DNA elements that act in concert with a promoter to increase transcription. Many enhancer sequences have been isolated from mammalian genes (hemoglobin, elastase, albumin, α-fetoprotein, and insulin), and eukaryotic cell viruses. The enhancer can be spliced into the vector at a position 5' or 3' to the heterologous coding sequence, but is typically inserted at a site 5' to the promoter.

Typically, the promoter, and if desired, additional transcription enhancing sequences are chosen to optimize expression in the host cell type into which the heterologous DNA is to be introduced (Scharf et al., 1994, Results Probl Cell Differ 20:125-62; Kriegler et al., 1990, Methods in Enzymol 185: 512-27). Optionally, the amplicon can also contain a ribosome binding site or an internal ribosome entry site (IRES) for translation initiation.

The vectors of the invention also favorably include sequences necessary for the termination of transcription and for stabilizing the mRNA, such as a polyadenylation site or a terminator sequence e.g., bovine growth hormone poly A signal. Such sequences are commonly available from the 5' and, occasionally 3', untranslated regions of eukaryotic or viral DNAs or cDNAs.

In one embodiment, In addition, as described above, the expression vectors optionally include one or more selectable marker genes to provide a phenotypic trait for selection of transformed host cells, in addition to genes previously listed, markers such as enzymatic markers e.g. dihydrofolate reductase or antibiotic markers, e.g. neomycin resistance are suitable for selection in eukaryotic cell culture.

The vector containing the appropriate DNA sequence as described above, as well as an appropriate promoter or control sequence, can be employed to transform a host cell permitting expression of the protein. While the vectors of the invention can be replicated in bacterial cells, most frequently it will be desirable to introduce them into mammalian cells, e.g., Vero cells, BHK cells, CEK cells, MDCK cell, 293T cells, COS cells, for the purpose of expression.

Additional Expression Elements

Most commonly, the genome segment encoding the influenza virus protein includes any additional sequences necessary for its expression, and/or translation into a functional viral protein. In other situations, a minigene, or other artificial construct encoding the viral proteins, e.g., an HA or NA protein, can be employed. In this case, it is often desirable to include specific initiation signals which aid in the efficient translation of the heterologous coding sequence. These signals can include, e.g., the ATG initiation codon and adjacent sequences. To insure translation of the entire insert, the initiation codon is inserted in the correct reading frame relative to the viral protein. Exogenous transcriptional elements and initiation codons can be of various origins, both natural and synthetic. The efficiency of expression can be enhanced by the inclusion of enhancers appropriate to the cell system in use.

If desired, polynucleotide sequences encoding additional expressed elements, such as signal sequences, secretion or localization sequences, and the like can be incorporated into the vector, usually, in-frame with the polynucleotide sequence of interest, e.g., to target polypeptide expression to a desired cellular compartment, membrane, or organelle, or into the cell culture media. Such sequences are known to those of skill, and include secretion leader peptides, organelle targeting sequences (e.g., nuclear localization sequences, ER retention signals, mitochondrial transit sequences), membrane localization/anchor sequences (e.g., stop transfer sequences, GPI anchor sequences), and the like.

Influenza Virus Vaccine

Historically, influenza virus vaccines have been produced in embryonated hens' eggs using strains of virus selected based on empirical predictions of relevant strains. More recently, reassortant viruses have been produced that incorporate selected hemagglutinin and neuramimidase antigens in the context of an approved attenuated, temperature sensitive master strain. Following culture of the virus through multiple passages in hens' eggs, influenza viruses are recovered and, optionally, inactivated, e.g., using formaldehyde and/or β-propiolactone. However, production of influenza vaccine in this manner has several significant drawbacks. Contaminants remaining from the hens' eggs are highly antigenic, pyrogenic, and frequently result in significant side effects upon administration. More importantly, strains designated for production must be selected and distributed, typically months in advance of the next flu season to allow time for production and inactivation of influenza vaccine. Attempts at producing recombinant and reassortant vaccines in cell culture have been hampered by the inability of any of the strains approved for vaccine production to grow efficiently under standard cell culture conditions.

The present invention uses reverse genetics, a method using a multi plasmid system in cell culture for producing recombinant and reassortant live attenuated viruses in culture which make it possible to rapidly produce vaccines corresponding to one or many selected antigenic strains of virus. Optionally, if desired, the viruses can be further amplified in Hens' eggs.

In the methods of the present invention, multiple plasmids, each incorporating a segment of an influenza virus genome are introduced into suitable cells, and maintained in culture at a temperature less than or equal to between 32-41° C. Typically, the cultures are maintained in a system, such as a cell culture incubator, under controlled humidity and $CO_2$, at constant temperature using a temperature regulator, such as a thermostat to insure that the temperature does not exceed 41° C.

Reassortant influenza viruses can be readily obtained by introducing a subset of vectors corresponding to genomic segments of a master backbone influenza virus, in combination with complementary segments derived from selected strains of interest (e.g., antigenic variants of interest). For example, for vaccine production, e.g., for production of a live attenuated vaccine, the master backbone donor virus strain may be selected for an attenuated phenotype, cold adaptation and/or temperature sensitivity. In this context, A/Guinea fowl/Hong Kong/WF10/99 or another avian influenza strain having the ts mutations and the genetic tag of the invention is selected as master backbone donor strains having desirable properties relevant to vaccine administration.

In one embodiment, plasmids incorporating the six internal genes of the influenza master backbone virus strain, (i.e., PB1, PB2, PA, NP, M, NS) are transfected into suitable host cells in combination with hemagglutinin and neuramimidase segments from a selected antigenically desirable strain, e.g., a strain predicted to cause significant local or global influenza infection. Following replication of the reassortant virus in cell culture at appropriate temperatures for efficient recovery, reassortant viruses is recovered. Optionally, the recovered virus can be inactivated using a denaturing agent such as formaldehyde or β-propiolactone.

Attenuated, Temperature Sensitive and Cold Adapted Influenza Virus Vaccines

In one aspect, the present invention is based on the incorporation of a genetic tag in the PB1 genome segment in addition to mutations underlying the ts phenotype such that the master backbone donor strain is attenuated.

In the present invention, the incorporation of a genetic tag in the PB1 genome segment is identified as functionally important in conferring the attenuated phenotype on the master donor strain virus. The ts mutations resulting in amino acid substitutions at positions $PB1^{391}$, $PB1^{581}$, $PB1^{661}$, $PB2^{265}$ described for human influenza A strain in Jin et al., 2003, Virology 306, 18-24 were not sufficient for attenuation of the avian influenza virus. The inventors found that the aspartic acid to glycine substitution at $NP^{34}$ is present in the NP gene of most avian influenza virus strains. Introduction of the genetic tag in combination with these mutations onto a wild-type avian influenza background results in virus with an attenuated phenotype. These changes appear to act in concert with one another to fully express the attenuated phenotype. This discovery permits the engineering of additional strains of attenuated avian influenza virus suitable for master donor viruses for the production of live attenuated influenza vaccines.

The genetic tag can be the specific sequence defined in SEQ ID NO:1, or any other random sequence. One or more genetic tag can be inserted either in frame or out of frame, in any of the influenza genes as long as viral replication is maintained. The genetic tag can be of any size as long as it does not destroy virus viability. The incorporation of the HA tag in frame with the C-terminus of PB1 provided a genetic marker to differentiate the vaccine strain from the field isolates (using real-time PCR, RT-PCR or a monoclaonal antibody specific for the genetic tag).

Influenza viruses incorporating the mutations and genetic tag of the invention are a feature of the invention regardless of the method in which they are produced. That is, the invention encompasses influenza strains including the mutations and genetic tag of the invention, e.g., any orthomyxoviruses with an amino acid substitution relative to wild type at one or more positions selected from among: $PB1^{391}$, $PB1^{581}$, $PB1^{661}$, $PB2^{265}$ and having a genetic tag in the PB1 gene.

Cell Culture

Propagation of the virus in culture is known to persons in the art. Briefly, the virus is grown in the media compositions in which the host cell is commonly cultured. Suitable host cells for the replication of influenza virus include, e.g., Vero cells, BHK cells, MDCK cells, 293 cells COS cells, and CEK cells, including 293T cells, COS7 cells. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

Procedures for maintaining mammalian cells in culture have been extensively reported, and are known to those of skill in the art. General protocols are provided, e.g., in Freshney (1983) Culture of Animal Cells: Manual of Basic Technique, Alan R. Liss, New York; Paul (1975) Cell and Tissue Culture, 5.sup.th ed., Livingston, Edinburgh; Adams (1980) Laboratory Techniques in Biochemistry and Molecular Biology-Cell Culture for Biochemists, Work and Burdon (eds.) Elsevier, Amsterdam. Additional details regarding tissue culture procedures of particular interest in the production of influenza virus in vitro include, e.g., Merten et al. (1996) Production of influenza virus in cell cultures for vaccine preparation. In Cohen and Shafferman (eds) Novel Strategies in Design and Production of Vaccines, which is incorporated herein in its entirety. Additionally, variations in such procedures adapted to the present invention are readily determined through routine experimentation.

Cells for production of influenza virus can be cultured in serum-containing or serum free medium. In some case, e.g., for the preparation of purified viruses, it is desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Regardless of the culture volume, in the context of the present invention, it is important that the cultures be maintained at a temperature less than or equal to 37° C. to insure efficient recovery of recombinant and/or reassortant influenza virus using the multi plasmid system described herein. For example, the cells are cultured at a temperature between about 25-37° C.

Introduction of Vectors into Host Cells

Vectors comprising influenza genome segments are introduced (e.g., transfected) into host cells according to methods well known in the art for introducing heterologous nucleic acids into eukaryotic cells, including, e.g., calcium phosphate co-precipitation, electroporation, microinjection, lipofection, and transfection employing polyamine transfection reagents. For example, vectors, e.g., plasmids, can be transfected into host cells, such as COS cells, MDCK, or 293T cells or combinations of COS or 293T cells and MDCK cells, using the polyamine transfection reagent TransIT-LT1 (Mirus) according to the manufacturer's instructions. Approximately 1 ug of each vector to be introduced into the population of host cells with approximately 2 ul of TransIT-LT1/ug of DNA diluted in 160 ul medium, preferably serum-free medium, in a total vol. of 200 ul. The DNA: transfection reagent mixtures are incubated at room temperature for 45 min followed by addition of 800 ul of medium. The transfection mixture is added to the host cells, and the cells are cultured as described above. Accordingly, for the production of recombinant or reassortant viruses in cell culture, vectors incorporating each of the 8 genome segments, (PB2, PB1, PA, NP, M, NS, HA and NA) are mixed with approximately 18 ul TransIT-LT1 and transfected into host cells. Optionally, serum-containing medium is replaced prior to transfection with serum-free medium, e.g., Opti-MEM I, and incubated for 4-6 hours.

Alternatively, electroporation can be employed to introduce vectors incorporating influenza genome segments into host cells. For example, plasmid vectors incorporating virus are favorably introduced into Vero cells using electroporation according to the following procedure. In brief, $5 \times 10^6$ Vero cells, e.g., grown in Modified Eagle's Medium (MEM) supplemented with 10% Fetal Bovine Serum (FBS) are resuspended in 0.4 ml OptiMEM and placed in an electroporation cuvette. Twenty micrograms of DNA in a volume of up to 25 ul is added to the cells in the cuvette, which is then mixed gently by tapping. Electroporation is performed according to the manufacturer's instructions (e.g., BioRad Gene Pulser II with Capacitance Extender Plus connected) at 300 volts, 950 microFarads with a time constant of between 28-33 msec. The cells are remixed by gently tapping and approximately 1-2 minutes following electroporation 0.7 ml MEM with 10% FBS is added directly to the cuvette. The cells are then transferred to two wells of a standard 6 well tissue culture dish containing 2 ml MEM, 10% FBS or OPTI-MEM without serum. The cuvette is washed to recover any remaining cells and the wash suspension is divided between the two wells. Final volume is approximately 3.5 mls. The cells are then incubated under conditions permissive for viral growth, e.g., at approximately 33° C. for cold adapted strains.

Recovery of Viruses

Viruses are typically recovered from the culture medium, in which infected (transfected) cells have been grown. Typically crude medium is clarified prior to concentration of influenza viruses. Common methods include filtration, ultrafiltration, adsorption on barium sulfate and elution, and centrifugation. For example, crude medium from infected cultures can first be clarified by centrifugation at, e.g., 1000-2000×g for a time sufficient to remove cell debris and other large particulate matter, e.g., between 10 and 30 minutes. Alternatively, the medium is filtered through a 0.8 um cellulose acetate filter to remove intact cells and other large particulate matter. Optionally, the clarified medium supernatant is then centrifuged to pellet the influenza viruses, e.g., at 15,000×g, for approximately 3-5 hours. Following resuspension of the virus pellet in an appropriate buffer, such as STE (0.01 M Tris-HCl; 0.15 M NaCl; 0.0001 M EDTA) or phosphate buffered saline (PBS) at pH 7.4, the virus is concentrated by density gradient centrifugation on sucrose (60%-12%) or potassium tartrate (50%-10%). Either continuous or step gradients, e.g., a sucrose gradient between 12% and 60% in four 12% steps, are suitable. The gradients are centrifuged at a speed, and for a time, sufficient for the viruses to concentrate into a visible band for recovery. Alternatively, and for most large scale commercial applications, virus is elutriated from density gradients using a zonal-centrifuge rotor operating in continuous mode. Additional details sufficient to guide one of skill through the preparation of influenza viruses from tissue culture are provided, e.g., in Furminger. Vaccine Production, in Nicholson et al. (eds) Textbook of Influenza pp. 324-332; Merten et al. (1996) Production of influenza virus in cell cultures for vaccine preparation, in Cohen & Shafferman (eds) Novel Strategies in Design and Production of Vaccines pp. 141-151, and U.S. Pat. No. 5,690,937. If desired, the recovered viruses can be stored at −80° C. in the presence of sucrose-phosphate-glutamate (SPG) as a stabilizer Methods and Compositions for Prophylactic Administration of Vaccines The term "immunogenic" refers to the ability of a substance to cause a humoral and/or cellular response, whether alone or when linked to a carrier, in the presence or absence of an adjuvant. "Neutralization" refers to an immune response that blocks the infectivity, either partially or fully, of an infectious agent. A "vaccine" is an immunogenic composition capable of eliciting protection against disease, whether partial or complete. A vaccine may also be useful for treatment of an infected individual, in which case it is called a therapeutic vaccine.

The term "therapeutic" refers to a composition capable of treating influenza virus infection. The term "effective amount" for a therapeutic or prophylactic treatment refers to an amount of epitope-bearing polypeptide sufficient to induce an immunogenic response in the individual to which it is administered, or to otherwise detectably immunoreact in its intended system (e.g., immunoassay). Preferably, the effective amount is sufficient to effect treatment, as defined above. The exact amount necessary will vary according to the application. For vaccine applications or for the generation of polyclonal antiserum/antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation.

Recombinant and reassortant viruses of the invention can be administered prophylactically in an appropriate carrier or excipient to stimulate an immune response specific for one or more strains of influenza virus. Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol, allantoic fluid from uninfected Hens' eggs (i.e., normal allantoic fluid "NAF") or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, etc.

Generally, the influenza viruses of the invention are administered in a quantity sufficient to stimulate an immune response specific for one or more strains of influenza virus. Preferably, administration of the influenza viruses elicits a protective immune response. Dosages and methods for eliciting a protective immune response against one or more influenza strains are known to those of skill in the art. For example, live attenuated influenza virus vaccine are provided in the range of 104-107 TCID50 (tissue culture dose 50), or about $10^5$-$10^8$ pfu (plaque forming units/ml) or about $10^3$ to $10^7$ egg infectious dose 50 per dose administered. Typically, the dose will be adjusted within this range based on, e.g., species, age, physical condition, body weight, sex, diet, time of administration, and other clinical factors. The prophylactic vaccine formulation is systemically administered, e.g., by subcutaneous or intramuscular injection using a needle and syringe, or a needleless injection device. Alternatively, the vaccine formulation is administered intranasally, either by drops, large particle aerosol (greater than about 10 microns), or spray into the upper respiratory tract. While any of the above routes of delivery results in a protective systemic immune response, intranasal administration confers the added benefit of eliciting mucosal immunity at the site of entry of the influenza virus. For intranasal administration, attenuated live virus vaccines are often preferred, e.g., an attenuated, cold adapted and/or temperature sensitive recombinant or reassortant influenza virus. While stimulation of a protective immune response with a single dose is preferred, additional dosages can be administered, by the same or different route, to achieve the desired prophylactic effect.

The vaccine can be administered by the oral, ocular, nasal, intradermal, intramuscular, in ovo or any other appropriate route which is shown to elicit an appropriate protective response in the vaccinated recipients. The vaccine can also be administered using a prime and boost regime if deemed necessary.

Optionally, the formulation for prophylactic administration of the influenza viruses, or subunits thereof, also contains one or more adjuvants for enhancing the immune response to the influenza antigens. Suitable adjuvants include: saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvants QS-21 and MF59 or any other adjuvant deemed suitable for poultry and livestock.

If desired, prophylactic vaccine administration of influenza viruses can be performed in conjunction with administration of one or more immunostimulatory molecules. Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the influenza viruses, or can be administered separately. Either the protein or an expression vector encoding the protein can be administered to produce an immunostimulatory effect.

In another embodiment, the vectors of the invention including influenza genome segments can be employed to introduce heterologous nucleic acids into a host organism or host cell, such as a mammalian cell, e.g., cells derived from a human subject, in combination with a suitable pharmaceutical carrier or excipient as described above. Typically, the heterologous nucleic acid is inserted into a non-essential region of a gene or gene segment, e.g., the M gene of segment 7. The heterologous polynucleotide sequence can encode a polypeptide or peptide, or an RNA such as an antisense RNA or ribozyme. The heterologous nucleic acid is then introduced into a host or host cells by producing recombinant viruses incorporating the heterologous nucleic, and the viruses are administered as described above.

Alternatively, a vector of the invention including a heterologous nucleic acid can be introduced and expressed in a host cell by co-transfecting the vector into a cell infected with an influenza virus. Optionally, the cells are then returned or delivered to the subject, typically to the site from which they were obtained. In some applications, the cells are grafted onto a tissue, organ, or system site (as described above) of interest, using established cell transfer or grafting procedures. For example, stem cells of the hematopoietic lineage, such as bone marrow, cord blood, or peripheral blood derived hematopoietic stem cells can be delivered to a subject using standard delivery or transfusion techniques.

Alternatively, the viruses comprising a heterologous nucleic acid can be delivered to the cells of a subject in vivo. Typically, such methods involve the administration of vector particles to a target cell population (e.g., blood cells, skin cells, liver cells, neural (including brain) cells, kidney cells, uterine cells, muscle cells, intestinal cells, cervical cells, vaginal cells, prostate cells, etc., as well as tumor cells derived from a variety of cells, tissues and/or organs. Administration can be either systemic, e.g., by intravenous administration of viral particles, or by delivering the viral particles directly to a site or sites of interest by a variety of methods, including injection (e.g., using a needle or syringe), needleless vaccine delivery, topical administration, or pushing into a tissue, organ or skin site. For example, the viral vector particles can be delivered by inhalation, orally, intravenously, subcutaneously, subdermally, intradermally, intramuscularly, intraperitoneally, intrathecally, by vaginal or rectal (cloacal in birds) administration, or by placing the viral particles within a cavity or other site of the body, e.g., during surgery.

The above described methods are useful for therapeutically and/or prophylactically treating a disease or disorder by introducing a vector of the invention comprising a heterologous polynucleotide encoding a therapeutically or prophylactically effective polypeptide (or peptide) or RNA (e.g., an antisense RNA or ribozyme) into a population of target cells in vitro, ex vivo or in vivo. Typically, the polynucleotide encoding the polypeptide (or peptide), or RNA, of interest is operably linked to appropriate regulatory sequences as described above in the sections entitled "Expression Vectors" and "Additional Expression Elements." Optionally, more than one heterologous coding sequence is incorporated into a single vector or virus. For example, in addition to a polynucleotide encoding a therapeutically or prophylactically active polypeptide or RNA, the vector can also include additional therapeutic or prophylactic polypeptides, e.g., antigens, co-stimulatory molecules, cytokines, antibodies, etc., and/or markers, and the like.

The methods and vectors of the present invention can be used to therapeutically or prophylactically treat a wide variety of disorders, including genetic and acquired disorders, e.g., as vaccines for infectious diseases, due to viruses, bacteria, and the like.

Kits

To facilitate use of the vectors and vector systems of the invention, any of the vectors, e.g., consensus influenza virus plasmids, variant influenza polypeptide plasmids, influenza polypeptide library plasmids, etc., and additional components, such as, buffer, cells, culture medium, useful for packaging and infection of influenza viruses for experimental or therapeutic purposes, can be packaged in the form of a kit. Typically, the kit contains, in addition to the above components, additional materials which can include, e.g., instructions for performing the methods of the invention, packaging material, and a container.

Manipulation of Viral Nucleic Acids and Proteins

In the context of the invention, influenza virus nucleic acids and/or proteins are manipulated according to well known molecular biology techniques. Detailed protocols for numerous such procedures, including amplification, cloning, mutagenesis, transformation, and the like, are described in, e.g., in Ausubel et al. Current Protocols in Molecular Biology (supplemented through 2000) John Wiley & Sons, New York ("Ausubel"); Sambrook et al. Molecular Cloning—A Laboratory Manual (2nd Ed.), Vol. 1-3, Cold Spring Harbor Laboratory, Cold Spring Harbor, N.Y., 1989 ("Sambrook"), and Berger and Kimmel Guide to Molecular Cloning Techniques, Methods in Enzymology volume 152 Academic Press, Inc., San Diego, Calif. ("Berger").

In addition to the above references, protocols for in vitro amplification techniques, such as the polymerase chain reaction (PCR), the ligase chain reaction (LCR), and other RNA polymerase mediated techniques (e.g., NASBA), useful e.g., for amplifying cDNA probes of the invention, are found in Mullis et al. (1987) U.S. Pat. No. 4,683,202; PCR Protocols A Guide to Methods and Applications (Innis et al. eds) Academic Press Inc. San Diego, Calif. (1990) ("Innis"); Arnheim and Levinson (1990) C&EN 36; The Journal Of NIH Research (1991) 3:81; Kwoh et al. (1989) Proc Natl Acad Sci USA 86, 1173; Guatelli et al. (1990) Proc Natl Acad Sci USA 87:1874; Lomell et al. (1989) J Clin Chem 35:1826; Landegren et al. (1988) Science 241:1077; Van Brunt (1990) Biotechnology 8:291; Wu and Wallace (1989) Gene 4: 560; Barringer et al. (1990) Gene 89:117, and Sooknanan and Malek (1995) Biotechnology 13:563. Additional methods, useful for cloning nucleic acids in the context of the present invention, include Wallace et al. U.S. Pat. No. 5,426,039. Improved methods of amplifying large nucleic acids by PCR are summarized in Cheng et al. (1994) Nature 369:684 and the references therein.

Certain polynucleotides of the invention, oligonucleotides can be synthesized utilizing various solid-phase strategies including mononucleotide- and/or trinucleotide-based phosphoramidite coupling chemistry. For example, nucleic acid sequences can be synthesized by the sequential addition of activated monomers and/or trimers to an elongating polynucleotide chain. See e.g., Caruthers, M. H. et al. (1992) Meth Enzymol 211:3.

In lieu of synthesizing the desired sequences, essentially any nucleic acid can be custom ordered from any of a variety of commercial sources, such as The Midland Certified Reagent Company (mcrc@oligos.com), The Great American Gene Company (www.genco.com), ExpressGen, Inc. (www.expressgen.com), Operon Technologies, Inc. (www.operon.com), and many others.

In addition, substitutions of selected amino acid residues in viral polypeptides can be accomplished by, e.g., site directed mutagenesis. For example, a genetic tag and other viral polypeptides with amino acid substitutions functionally correlated with desirable phenotypic characteristic, e.g., an attenuated phenotype, cold adaptation, temperature sensitivity, can be produced by introducing specific mutations into a viral nucleic acid segment encoding the polypeptide. Methods for site directed mutagenesis are well known in the art, and described, e.g., in Ausubel, Sambrook, and Berger, supra. Numerous kits for performing site directed mutagenesis are commercially available, e.g., the Chameleon Site Directed Mutagenesis Kit (Stratagene, La Jolla), and can be used according to the manufacturers instructions to introduce, one or more amino acid substitutions and/or a genetic tag into a genome segment encoding an influenza virus polypeptide.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following MATERIALS AND METHODS were used in the examples that follow.

Viruses and Cells

A/Guinea Fowl/Hong Kong/WF10/99 (H9N2) (WF10) and A/WSN/33 (H1N1) (WSN) were kindly provided from the repository of St. Judes Children's Research Hospital by Dr. Robert Webster, Memphis, Tenn.; the influenza A/Chicken/Delaware/VIVA/04 (H7N2) (CK/04) was obtained from Mr. Dennis Senne at the National Veterinary Laboratory Services, USDA, Ames, Iowa; the highly pathogenic influenza A/Vietnam/1203/04 (H5N1) (A/VN/1203/04) was obtained from the repository at the Centers for Disease Control and Prevention (CDC), Atlanta, Ga. The viruses were propagated in 10-day-old embryonated SPF chicken eggs at 35° C. and stored at −70° C. The viruses were titrated to determine the egg infectious dose 50 ($EID_{50}$) by the Reed and Muench method (Hierholzer and Killington, 1996, Virus isolation and quantitation, pp. 25-46. IN B. W. Mahy and H. I. Kangro (ed.), Virology methods manual. Academic Press, London, United Kingdom.) The HA titers were determined by hemagglutination assay. Madin-Darby canine kidney (MDCK) cells were maintained in Modified Eagle's medium (MEM) (Sigman-Aldrich, St. Louis, Mo.) containing 5% or 10% fetal bovine serum (FBS) (Sigma-Aldrich). 293-T human embryonic kidney cells were cultured in Opti-MEM I (GIBCO, Grand Island, N.Y.) containing 5% or 10% FBS. During and after transfection, cells were maintained in Opti-MEM I (GIBCO, Grand Island, N.Y.) containing 5% FBS. Chicken embryo kidney cells (CEK) were isolated from 18-day-old chicken embryos and maintained in medium M199 (GIBCO, Grand Island, N.Y.) containing 5% FBS and 2.5% chicken serum. All cells were maintained at 37° C. in 5% $CO_2$. The titer of stock viruses was measured by plaque assay on MDCK cells at 37° C. or 32° C. or by egg infectious dose 50 ($EID_{50}$) as described (Reed, and Muench, 1938, Am. J. Hyg. 37, 493). All in vitro studies using HPAI virus were performed in an enhanced biosafety level-3 (BSL-3) facility approved by the USDA.

Cloning and Generation of Viruses by Reverse Genetics

The HA and NA genes of CK/04 (H7N2) were cloned using a set of universal primers as described (Hoffmann et al., 2002, Vaccine 20, 3165-3170; Hoffmann et al., 2001, Arch. Virol. 146, 18-24). Cloning of the eight genes of WF10 virus has been described in separate studies (Perez et al., 2003, Avian Dis. 47, 1114-1117). The H56, (with the deletion of the polybasic amino acid sequence) and N1 genes from A/Vietnam/1203/04 were cloned from the 6PR8:2 H5ΔN1 recombinant virus, a kind gift from Dr. Ruben Donis, CDC. Cloned genes were sequenced and compared to the corresponding viral sequences to determine that the clones did not carry spurious mutations. Sequences were generated using the Big Dye Terminator v3.1 Cycle Sequencing kit 1 (Applied Biosystems, Foster City, Calif.) and a 3100 Genetic Analyzer (Applied Biosystems), according to the instructions of the manufacturer. The ts mutations in PB1 and PB2 were introduced by site-directed mutagenesis using a commercially available kit (Stratagene, La Jolla, Calif.). The PB1 gene of the WF10 virus was further modified by PCR incorporating an HA tag sequence (8 amino acids derived from the influenza H3 HA protein sequence, tag) in-frame with the PB1 open reading frame while preserving the essential assembly sequences (Muramoto et al., 2006, J. Virol. 80, 2318-2325). The HA tag was incorporated in the context of wild type and ts PB1 sequences as indicated in the text and in FIG. 1. Thus, the C-terminus of the PB1 gene at the HA tag junction contains the following sequence, EDMYPYDVPDY ASRICSTIEELRRQK-C-terminus (SEQ ID NO:2), in which the underlined amino acids correspond to artificially introduced amino acids, those in italics correspond to the HA tag and the rest to PB1. For in vitro studies, the HA gene derived from influenza A/Mallard/Alberta/24/01 (H7N3) (Mal/01) adapted to MDCK cells, a kind gift from Dr. Webster, was used because it provides a large-plaque phenotype in MDCK cells in the presence of trypsin.

Viruses were rescued as described (Hoffmann et al., 2000, PNAS USA 97, 6108-6113). Briefly, the day before transfection, confluent 293T and MDCK cells in a 75 $cm^2$ flask were trypsinized, and 10% of each cell line was mixed in 18 ml OptiMEM I; 3 ml of this cell suspension was seeded into one well of a six-well plate. The next day, 1 µg of each plasmid (~8 µg) was mixed with 18 µl of TransIT LT-1 (Mirus, Madison, Wis.). After 45 min incubation at room temperature, the mixture was added to the cells. Six hours later, the DNA-transfection mixture was replaced by Opti-MEM I. Thirty hours after transfection, 1 ml of Opti-MEM I containing 1 µg/ml TPCK-trypsin was added to the cells. Viruses were propagated in 10-day-old embryonated chicken eggs, and titrated by $EID_{50}$. The recovery of recombinant viruses was verified by sequencing using specific primers. The wild type and HA tagged viruses were differentiated by RT-PCR using the specific primer sets PB1-2147F (SEQ ID NO:6) and HAtagR (SEQ ID NO:5), and PB1-2147F and PB1-2431R (SEQ ID NO:7), shown in FIG. 1. Genetic stability of the mutant viruses was evaluated by serial passage (10 times) of virus stocks at 1:10,000 dilution in 10-day old embryonated eggs.

Plaque Assays and Immunostaining

The ca/ts phenotype of the recombinant viruses was examined by plaque assay in MDCK cells and CEK cells at 32° C., 37° C., 39° C., and 41° C. Confluent cell monolayers in 6-well plates were infected with 10-fold dilutions of virus in a total volume of 0.4 ml of PBS for 1 h at 37° C. Cells were washed twice with PBS and covered with an overlay of MEM containing 0.9% agar, 0.02% BSA, 1% glutamine, and 1 µg/ml TPCK trypsin. The plates were then incubated at 32° C., 37° C., 39° C., and 41° C. under 5% $CO_2$. After 3 days of incubation at 37° C., 39° C. and 41° C., or 4 days at 32° C., the overlays were removed and the cells were fixed with 4% paraformaldehyde and permeabilized with 0.2% Triton X-100. The potential endogenous peroxidase activity was destroyed by incubation with 1% $H_2O_2$-methanol. After blocking with 1% BSA in PBS, the cells were incubated with mouse anti-WF10 polyclonal antibody prepared in our laboratory, followed by incubation with peroxidase-conjugated goat-anti-mouse IgG (Jackson Immuno Research, West Grove, Pa.). The viral antigen was visualized by incubating the cells in a solution of aminoethylcarbazol (Dakocytomation, Carpinteria, Calif.). The size and number of plaques were obtained at each temperature and compared to determine the is phenotype of each virus. The non-permissive temperature was defined as the lowest temperature that had a titer reduction of 100-fold or greater compared to 37° C.

Western Blot

MDCK cells grown in 6-well plates were infected with the recombinant viruses and A/Memphis/98 (H3N2) as control. After infection the cells were trypsinized and collected by centrifugation. The cells were washed once with ice-cold PBS, resuspended in 50 µl of PBS and mixed with 100 µl Laemmli sample buffer (Bio-Rad, Hercules, Calif.). The samples were then boiled for 5 min, and centrifuged at 13,000 g for 3 min at 4° C. For immunoblotting, the cell lysates were fractionated by 10% SDS-PAGE gels, and the proteins were transferred onto nitrocellulose membrane (Bio-Rad, Hercules, Calif.) for immunoblot analysis. The membranes were blocked in 5% non-fat milk in PBS for 1 h at room temperature, and then incubated for 1 h with primary antibodies for NP (mouse anti-WF10 polyclonal antibody), M1 [mouse anti-M1 monoclonal antibody (ATCC, Manassas, Va.)], actin [mouse anti-actin monoclonal antibody (Chemicon, Temecula, Calif.)] or HA tag [rat anti-HA monoclonal antibody (Roche Diagnostics, Indianapolis, Ind.)]. Immunoblots were washed 3 times with PBS containing 0.05% Tween 20, and subsequently incubated with a 1:10,000 dilution of goat anti-mouse or goat anti-rat IgG conjugated to horseradish peroxidase (Jackson Immuno Research, West Grove, Pa.). Finally, the membranes were washed three times and visualized by enhanced chemiluminescence (Pierce, Rockford, Ill.).

Virus Replication and Transmission Study

Animal studies were approved by the Animal Care and Use Committee of the University of Maryland, College Park. Three 3-week old White Leghorn chickens (Charles River Laboratories, MA) were inoculated intraocularly, intranasally, orally, and intratracheally with $5 \times 10^6$ $EID_{50}$ of avian influenza virus contained in 1 ml inoculum. 8 drops (0.2 ml) were introduced through the eyes and nares, and 0.8 ml of the virus dilution was equally distributed between oral and tracheal inoculations. The day after infection, 3 naïve birds were introduced to the same cage with the infected birds, in order to monitor the transmissibility of the virus. Tracheal and cloacal swabs were collected from both the infected and contact birds at days 1, 3, 5, 7, and 9 post-infection (DPI). The samples were stored in glass vials diluted in 1 ml freezing medium (50% glycerol PBS containing antibiotics) and titrated for infectivity in 10-day embryonated chicken eggs. Sera were collected 2 weeks after infections and tested for antibodies against the HA by hemagglutination inhibition (HI) test. In a separate study, three 3-week old White Leghorn chickens were infected as described above, except that an additional 0.5 ml of the virus dilution was administrated through the cloaca. At 3 days post-infection, tracheal and cloacal swabs were collected, the birds were sacrificed, lung homogenates were prepared, and the virus was titrated by inoculating 10-day old embryonated eggs. Birds were observed and scored daily for clinical signs of illness. Experiments were carried out under BSL2 conditions.

Dose Dependent Immunization and Low Pathogenic H7N2 Challenge Study 2 week-old White Leghorn chickens were immunized with 50, 500, 5000, $5 \times 10^4$, $5 \times 10^5$ or $1 \times 10^6$ $EID_{50}$ vaccine virus (6attWF10:2ckH7N2) in 0.5 ml of diluent, through intraocular, intranasal, oral, and intratracheal inoculation. At 3 and 5 days post-vaccination, tracheal swabs from all the vaccinated birds were collected. The presence of both the is mutation and the HA tag in the recombinant vaccine virus were confirmed by RT-PCR and sequencing as described above. Two weeks after vaccination, chickens were challenged by intranasal inoculation with $5 \times 10^5$ $EID_{50}$ of influenza CK/04 virus, corresponding to 500 chicken infectious dose 50 (500 $CID_{50}$) (data not shown). A group of eight chickens immunized with PBS only, served as challenge control for virus shedding. To evaluate the level of virus shedding, both tracheal and cloacal swabs were collected at 3, 5, 7 days post-challenge. Sera were collected 2 weeks after vaccination and 2 weeks after challenge, respectively. Sera were treated with receptor destroying enzyme (Denka Seiken Co., Tokyo, Japan), and tested for antibodies against 8 HA units of Ck/04 by hemagglutination inhibition (HI) assay following the World Health Organization (WHO) protocol.

Immunization and Highly Pathogenic H5N1 Challenge Study

In ovo vaccination of 18 day-old embryonated SPF chicken eggs were performed as described (Toro et al., 2007, Vaccine 25, 2886-2891). Briefly, eggs were candled; and a small hole was made through the air cell with a drill. Eggs were injected with 100 µl of high dose ($10^6 EID_{50}$) or low dose ($10^4 EID_{50}$) live attenuated vaccine (6attWF10:2 H5ΔN1) or PBS only using a 21-gauge needle at the depth of one inch. At 2 weeks post-hatching, a boost vaccination was performed, when indicated. Eight chickens from each of the in ovo vaccinated groups were boosted with either high dose ($10^6 EID_{50}/0.5$ ml) or low dose ($10^4 EID_{50}/0.5$ ml). Serum was collected from jugular or wing vein on a weekly basis for the determination of HI antibody titers. At 4 week-old, the challenge was performed by intranasal inoculation of $1 \times 10^5 EID_{50}/0.2$ ml of A/VN/1203/04 (H5N1) virus. Two groups of eight chickens that were immunized in ovo with $10^6$ $EID_{50}$ single dose vaccine were kept until 9 or 12 week-old, at which time the chickens were challenged with $3 \times 10^6 EID_{50}/0.6$ ml of A/VN/1203/04 virus. Tracheal and cloacal swabs were collected on days 2, 4 and 7 post-challenge for virus titration. After challenge the birds were observed and scored daily for morbidity and mortality for the next 14 days. The survivors were bled and humanely sacrificed at 14 days after challenge. Hemagglutination inhibition (HI) antibody titers were determined against 8 HA units of the A/VN/1203/04 virus. Challenge studies with the HPAI H5N1 virus were performed in an enhanced biosafety level-3 facility approved by the USDA.

Animal Studies

Five-week-old female BALB/c mice (Charles River, Wilmington, Mass.) were anesthetized with isoflurane before intranasal inoculation with 50 µl of virus suspension. Mouse lethal dose ($MLD_{50}$) for the WSN, A/VN/1203/04 and recombinant viruses, were calculated using groups of 4 mice inoculated intranasally with various doses ranging from $10^0$ to $10^6$ PFU/mouse. Clinical symptoms, body weight and mortality of mice were monitored and recorded for the subsequent 14 or 21 days as indicated. Animal studies using H1N1 recombinant viruses were conducted under biosafety level-2 (BSL-2) conditions; whereas those with H5N1 (HPAI) recombinants were performed under BSL-3 conditions with USDA approval. Animal studies were performed according to protocols approved by the Animal Care and Use Committee of the University of Maryland, College Park.

Evaluation of the Protective Efficacy of Recombinant Viruses

To evaluate the induction of immune responses and protective capacity of the recombinant viruses against wild-type WSN virus challenge, mice (7 mice/group) before they were 4-weeks old were immunized intranasally with recombinant viruses in a 50 µl volume at various doses ranging from $10^1$ to $10^6$ PFU/mouse. To evaluate the induction of immune responses and protective capacity of the recombinant viruses against wild-type HPAI H5N1 virus challenge, mice (10 mice/group) were immunized intranasally with recombinant viruses in a 50 µl volume at $10^6$ $EID_{50}$/mouse. All mock-immunized mice received 50 µL PBS. At 21 days post inoculation (dpi), sera were collected for antibody titration. At 21 dpi, mice were challenged with $10^5$ PFU (20 $MLD_{50}$) of WSN virus or 20 $EID_{50}$ (20 $MLD_{50}$) of HPAI H5N1 virus by the intranasal route. Alternatively, mice receive a boost immunization at 21 days post vaccination and 21 days later were challenged as described above. At 3 days post challenge (dpc) (and 6, where indicated), 3 mice/group were sacrificed and lungs collected and homogenized to measure virus titers. Lung homogenates were prepared in PBS and frozen at −70° C. until use. Virus titers in lung homogenates were determined by plaque assay (WSN) or tissue culture infectious dose 50 ($TCID_{50}$) (HPAI H5N1) on MDCK cells at 37° C.

Microneutralization Assays

Receptor destroying enzyme (RDE) treated sera were serially diluted 2-fold in PBS and then placed into 96 well U bottom microtiter plates (50 µl/well). Following the addition of 50 µl containing 100 TCID50 of virus diluted in PBS into each well, plates were mixed and incubated at 37° C. for 1 h. Subsequently, the serum:virus mixture (100 µl) was added to a monolayer of MDCK cells in 96 well plate. The plate was incubated at 4° C. for 15 min and then transferred to 37° C. for 45 min. After incubation, the serum:virus mixture was removed and 200 µl of Opti-MEM I with 1 µg/ml of TPCK-trypsin was added. The cells were incubated at 37° C. for 3 days and an HA assay was performed. The neutralizing antibody titers were expressed as the reciprocal of the highest dilution of the sample that completely inhibited hemagglutination. HA assays were performed following WHO/OIE standard assays.

Example 1

The ts Phenotype of the PB1 and PB2 Genes in the ca/ts/att A/Ann Arbor/6/60 Can be Transferred to an Avian Influenza Virus The ts phenotype of the A/Ann Arbor/6/60 (H2N2), the master donor of the cold-adapted human influenza virus, has been mapped to three amino acid mutations in PB1 (K391E, E581G, A661T), one in PB2 (N265S), and one in NP (D34G) (Jin et al., 2003, Virology 306, 18-24). Viruses carrying these mutations can replicate efficiently in vitro at a temperature of about 33° C. but are restricted for growth at 38-39° C. The attenuation phenotype is observed in vivo in the ferret model in which the mutant viruses establish limited infection in the upper respiratory tract but not in the lower respiratory tract (Jin et al., 2004, J. Virol. 78, 995-998). Sequence alignment of the PB1 and PB2 genes revealed that avian influenza viruses do not carry the amino acid mutations found in the ca/ts A/Ann Arbor/6/60 strain and thus are not expected to have a ca/ts phenotype (not shown). The WF10 used in our study already contains the D34G mutation found in the NP gene of ca/ts A/Ann Arbor/6/60 strain. In fact, of the approximately 2,000 avian influenza NP sequences available in GenBank, the vast majority of them encode for glycine or serine at position 34, with a single virus strain [A/chicken/Korea/38349-96323/96 (H9N2)] encoding for aspartic acid in such position. This observations suggests that the former two amino acids may favor the adaptation of influenza viruses to eggs or avian species. In contrast, the NP gene of most human influenza viruses (more than 2,500 sequences are available in GenBank) encode for aspartic acid at position 34, although the occasional emergence of seasonal strains carrying a glycine is not uncommon.

To determine whether the ts mutations found in ca/ts A/Ann Arbor/6/60 strain would impart the same ts phenotype to an avian influenza virus, the PB1 and PB2 genes of WF10 were mutated accordingly (FIG. 1). Both ts mutant and wild-type were rescued carrying the H7 HA gene from a MDCK cell-adapted Mal/01 (H7N3) virus. The HA gene from the cell-adapted Mal/01 (H7N3) virus provides a large-plaque phenotype in MDCK cells. The mutant virus was designated as 7tsWF10:1malH7 whereas its wild type counterpart was labeled as 7WF10:1malH7. We tested the ability of these viruses to form plaques at different temperatures in MDCK cells (data not shown). Plaque assays were carried out and after 3 days post-infection at 37° C., 39° C., and 41° C. or 4 days post-infection at 32° C., cells were immunostained with mouse anti-WF10 polyclonal antibody. Compared with the wild type virus, the 7tsWF10:1malH7 recombinant virus showed a 100-fold reduction in virus titer at 39° C. relative to 37° C. At 41° C., the WT showed pinpoint plaques, whereas none of the mutants were able to form plaques at this temperature, even at low dilutions ($10^{-3}$, data not shown).

We wanted also to confirm whether the ts phenotype imparted by the mutations in PB1 and PB2 of the WF10 virus could be maintained in cells of avian origin. Plaque assays were performed using primary chicken embryonic kidney (CEK) cells. We found that the wild type and ts viruses formed bigger plaques and grew to higher titers in CEK cells than in MDCK cells. This observation is consistent with previous studies that indicate that CEK cells are a better substrate than MDCK cells to propagate avian influenza viruses (Sugimura et al., 2000, J. Vet. Med. Sci. 62, 659-660). The pattern of restriction of the ts mutant viruses in CEK cells at different temperatures was similar to the one observed in MDCK cells. It is important to note that there was an overall improvement in the ability of wild type and mutant viruses to replicate at 39° C. and 41° C. in CEK cells. Interestingly, although the 7tsWF10:1malH7 virus could not form plaques in MDCK cells at 41° C., it formed small sized plaques at 41° C. in CEK cells. Our results suggest that cellular factors could be contributing to the overall effect on the ts phenotype in these viruses. In our studies, the ts phenotype was more evident in MDCK cells than in CEK cells. Interestingly, the ts viruses were not greatly attenuated in chickens, i.e. titers in the trachea and lungs were statistically indistinguishable from those obtained in infections with wild type viruses (Table 3). Thus, additional modifications in the genome of the avian influenza viruses were needed in order to produce a live attenuated avian influenza virus for birds.

Example 2

An Additional Genetic Modification in the PB1 Gene of an Avian Influenza Virus Enhances the ts Phenotype In Vitro and the att Phenotype in Birds Using reverse genetics, we had previously generated a laboratory strain of influenza A/WSN/33 (H1N1) carrying a recombinant PB1 gene in which the C-terminus of PB1 was fused to an 8 amino acid HA epitope tag (PB1tag) (Perez, unpublished). The growth kinetics of the 7WSN:1PB1tag virus was slower than the wild type virus, although it reached titers similar to those obtained with the wild type strain at 37° C. and displayed a is phenotype at 39° C. (not shown). We wanted to determine if avian influenza viruses carrying a PB1tag recombinant gene in the context of other ts mutations would be attenuated in birds. We modified the PB1 of the wild type WF10 virus to carry just the HA epitope tag (tag) or the HA tag with the ts loci (att) (FIG. 1). The new recovered viruses were labeled as 7tagWF10:1malH7 and 7attWF10: 1malH7, respectively. The recovery of the recombinant viruses was verified by sequence analysis using viruses grown in eggs. In addition, the recovery of the HA tagged viruses was demonstrated by RT-PCR. Using the pair of primers, PB1-2147 and HA tagR (data not shown), a 150 bp PCR product could be specifically amplified only in 7tagWF10: 1malH7 and 7attWF10:1malH7 viruses but not in the 7tsWF10:1malH7 or 7WF10:1malH7. A second control PCR product was amplified, using the primer pair, PB1-2147F and PB1-2341R. The viruses with the HA tag showed a band of slower migration in an agarose gel due to the larger size of the products containing estrogenic sequences. The in-frame cloning of the HA tag in PB1 also allowed the detection of the PB1 protein using a monoclonal antibody against the HA tag (data not shown). The expression of the PB1HA fusion protein of approximately ~90 kDa was readily detected from MDCK cell extracts prepared 16 h post-infection at multiplicity of infection (MOI) of 1 with 7tagWF10:1malH7 and 7tattWF10:1malH7 viruses but not with either 7tsWF10: 1malH7 or 7WF10:1malH7s viruses.

The ca and ts phenotypes of the HA tagged viruses were examined by plaque assay in MDCK and CEK cells at various temperatures (32° C., 37° C., 39° C. and 41° C.) as described above. We found that the HA epitope alone was sufficient to confer a ts phenotype to these viruses in MDCK at 39° C. (data not shown). Moreover, the HA tagged virus (7tagWF10: 1malH7) failed to form plaques at 41° C., even at $10^{-3}$ dilution. Albeit limited, the ts phenotype was also observed in CEK cells at 41° C., it formed much smaller sized plaques at this temperature compared to the wild type virus. More importantly, the double mutant 7attWF10:1malH7 virus was completely restricted at 39° C. and 41° C. in MDCK cells, and at 41° C. in CEK cells, showing >10,000-fold reduction in virus titers compared to growth at 32° C. Thus, our strategy resulted in an avian influenza virus with the typical characteristics of a ts strain. These observations were confirmed by analyzing the effect of viral protein synthesis at different temperatures in MDCK and CEK cells. The Western blot analysis examining the accumulation of one of the early viral proteins, NP, and the late viral protein, M1, at 6 h post-infection in cells extracts previously infected with the indicated influenza viruses at an MOI of 10 results are as follows (data not shown). In MDCK-infected cells, complete inhibition of protein synthesis for the ts, tag, and att mutant viruses was observed at 41° C. In CEK cells, inhibition of viral protein synthesis at 41° C. is only observed with the double mutant tsHA virus. Interestingly, viral protein synthesis at other temperatures (37° C. and 39° C.) achieved levels similar to the wild type virus in both cell types, except for the att virus in MDCK cells at 39° C. These results suggest that the ts restriction and the resulting small plaque phenotype are not due exclusively to alterations of viral protein synthesis at higher temperatures. The ts loci may be also affecting other viral functions, such as nuclear export or assembly. Taken together, with the incorporation of the HA tag in the PB1 protein, we were able to enhance the ts phenotype of avian influenza virus, making a live-attenuated (att) influenza virus.

The viruses harboring either the HA tag or ts mutations were not as attenuated in cell cultures at higher temperature as the double mutant att virus, suggesting that the HA tag and ts mutations worked synergistically to contribute to the ts effect (Table 1). Further analysis revealed that the HA tag virus with the triple mutation (PB1$^{391E581G661T}$tag/PB2 wt) or double ts mutations (PB1$^{391E581G}$tag/PB2 wt) in PB1, display an attenuation phenotype that resembles the double mutant 7attWF10:1malH7, i.e. it failed to form plaques at 41° C. in CEK cells using a $10^{-3}$ dilution. In contrast the HA-tag virus with the 265S mutation in PB2 (PB1tag/PB2$^{265}$) shows only about 1.4 $\log_{10}$ PFU/ml reduction in virus titer at 41° C. compared to growth at 37° C. All other ts/tag combinations have an intermediate ts phenotype compared to the 7tsWF10: 1malH7 virus.

In order to determine whether our strategy would result in an attenuated virus for birds with potential as a vaccine candidate, we tested the transmission and replication of recombinant viruses carrying the surface proteins of a low pathogenic virus, Ck/04 (H7N2). The Ck/04 (H7N2) is an isolate that was implicated in an outbreak of influenza in poultry in Maryland in 2004. We recovered reassortant viruses that contained the HA and NA genes derived from Ck/04 and different sets of mutant or wild type genes derived from the WF10

TABLE 1

Replication of recombinant viruses at various temperatures in CEK cells[a].

| Viruses | Virus titer ($\log_{10}$PFU/ml)[d] | | |
|---|---|---|---|
| | 37° C. | 41° C. | 37° C./41° C. |
| PB1$^{391E, 581G, 661T}$tag/PB2$^{265S}$ (7attWF10:1malH7) | 8.8 | <3.0[b] | >5.8 |
| PB1$^{391E, 581G, 661T}$/PB2 | 8.6 | 8.2 | 0.4 |
| PB1$^{391E, 581G, 661T}$/PB2$^{265S}$ (7tsWF10:1malH7) | 9.3 | 7.3 | 2.0 |
| PB1tag/PB2 (7tagWF10:1malH7) | 8.8 | 8.1 | 0.7 |
| PB1tag/PB2$^{265S}$ | 7.0 | 5.6 | 1.4 |
| PB1$^{391E581G661T}$tag/PB2 | 8.7 | <3.0[b] | >5.7 |
| PB1$^{391E}$tag/PB2 | 8.2 | 6.7[c] | 1.5 |
| PB1$^{581G}$tag/PB2 | 8.6 | 7.5[c] | 1.1 |
| PB1$^{661T}$tag/PB2 | 8.2 | 7.6[c] | 0.6 |
| PB1$^{391E661T}$tag/PB2 | 8.0 | 6.5[c] | 1.5 |
| PB1$^{391E581G}$tag/PB2 | 8.6 | <3.0[b] | >5.6 |
| PB1$^{581G661T}$tag/PB2 | 8.2 | 6.9[c] | 1.3 |

[a]Confluent CEK cell monolayers in 6-well plates were infected with 10-fold dilutions of viruses. The plaque counts were obtained at each of the temperatures.
[b]A titer of <3.0 $\log_{10}$ PFU/ml indicates that no plaque was detected at $10^{-3}$ dilutions. The non-permissive temperature was defined as the lowest temperature that had a titer reduction of 100-fold or greater compared to 37° C. Titers that define the shut-off temperature are shown in bold.
[c]Indicates reduction in plaque size and weaker immunostaining compared to the same recombinant virus at 37° C.
[d]The virus titer represents the average of two independent experiments.

virus. The recombinant virus containing the surface genes of Ck/04 and the internal genes of the wild type WF10 virus (6WF10:2ckH7N2) replicates and transmits efficiently to naïve contact chickens (Table 2). In contrast, no evidence of transmission was observed with any of the mutant backbones tested, namely the ts, HA or att. No virus shedding and no seroconversion were detected in naï birds that were placed in contact with chickens infected with any of the mutant viruses (Table 2).

The att phenotype of the ca/ts/att human influenza virus has been arbitrarily defined as limited virus replication and lack thereof, respectively in the upper respiratory tract and the lower respiratory tract of the ferret (Belshe et al., 1998, N. Engl. J. Med. 338, 1405-1412; Maassab et al., 1982, J. Infect. Dis. 146, 780-790). We extended this definition to include birds and to determine whether the combination of the ts and HA tag mutations were sufficient, to attenuate the virus, specifically in chickens. Since influenza virus replication can be established both in the respiratory and intestinal tracts in land-based birds, we evaluated cloacal swabs for the presence of virus after inoculating the virus directly through cloaca. 3 week-old White Leghorn chickens were infected with $5\times10^6$ $EID_{50}$ of virus through the intraocular, intranasal, oral, intratracheal and cloacal route. At 3 days post-infection, tracheal and cloacal swabs were collected, the birds were then sacrificed, lung tissues were harvested, and the viruses were titrated. Our results show that the double mutant 6attWF10:ckH7N2 virus was attenuated in chickens (Table 3). The double mutant virus showed a ~10-fold reduction in virus titers in tracheal swabs compared to the wild type virus and failed to replicate in the lower respiratory tract (lung). Only traces of the double mutant virus were detected in cloacal swabs in two out of the six infected chickens. This is probably due to the fact that the temperature in both intestinal tract and lower respiratory tract of birds is close to 41° C., at which temperature the att virus fail to grow in CEK cells. Our results suggest that it is possible to create an avian influenza virus with an attenuated phenotype in birds, i.e. a virus with only limited replication in the upper respiratory tract, unable to cause disease, unable to transmit and shed in feces and one that could potentially protect against field infections if it mounts an adequate immune response.

Example 3

A single Vaccination Dose of the 6attWF10:2ckH7N2 Virus Protects Chickens from Challenge with a Low Pathogenic avian H7 Influenza Virus In order to evaluate protective efficacy of the modified live attenuated virus at different doses, 2 week-old chickens were vaccinated intranasally, intraocularly, orally, and intratracheally with 50, 500, 5000, $5\times10^{14}$, $5\times10^5$ or $10^6 EID_{50}$ of the 6attWF10:2ckH7N2 virus (Table 4). At 2

TABLE 2

Transmission studies of the recombinant viruses in chickens[a]

| Virus/groups | | Number with positive tracheal swab/total N | | | | | Seroconversion[c] (seroconverted/total) |
|---|---|---|---|---|---|---|---|
| | | Day 1 | Day 3 | Day 5 | Day 7 | Day 9 | |
| 6WF10:2ckH7N2 | Inoculated chicken[b] | 3/3 | 3/3 | 2/3 | 0/3 | 0/3 | 3/3 |
| | Contact | 0/3 | 0/3 | 2/3 | 2/3 | 0/3 | 2/3 |
| 6tsWF10:2ckH7N2 | Inoculated chicken[b] | 3/3 | 3/3 | 3/3 | 0/3 | 0/3 | 3/3 |
| | Contact | 0/3 | 0/3 | 0/3 | 0/3 | 0/3 | 0/3 |
| 6tagWF10:2ckH7N2 | Inoculated chicken[b] | 3/3 | 3/3 | 1/3 | 0/3 | 0/3 | 3/3 |
| | Contact | 0/3 | 0/3 | 0/3 | 0/3 | 0/3 | 0/3 |
| 6attWF10:2ckH7N2 | Inoculated chicken[b] | 3/3 | 3/3 | 2/3 | 0/3 | 0/3 | 3/3 |
| | Contact | 0/3 | 0/3 | 0/3 | 0/3 | 0/3 | 0/3 |

[a]Three 3-week old White Leghorn chickens were inoculated intraocularly, intranasally, orally, and intratracheally with $5 \times 10^6$ $EID_{50}$ dose of virus. The next day after infection, 3 naïve birds were introduced in the same cage as the infected birds. Tracheal and cloacal swabs were collected from chickens every two days for 9 days after inoculation.
[b]Cloacal swabs were negative for virus isolation.
[c]Chickens were sacrificed 2 weeks after inoculation and sera were harvested. Seroconversion was confirmed by hemagglutination inhibition (HI) test.

TABLE 3

Replication of the reassortant viruses in chickens[a]

| | Virus titer in: | | |
|---|---|---|---|
| Viruses | Lungs [$Log_{10}(EID_{50}/g)$] | Trachea [$Log_{10}(EID_{50}/ml)$] | Cloaca [$Log_{10}(EID_{50}/ml)$] |
| 6WF10:2ckH7N2 | 3.6 ± 0.5 | 3.6 ± 0.8 | 4.0 ± 1.0 |
| 6tsWF10:2ckH7N2 | 3.8 ± 0.6 | 3.2 ± 0.6 | 4.0 ± 1.0 |

TABLE 3-continued

Replication of the reassortant viruses in chickens[a]

| Viruses | Virus titer in: | | |
|---|---|---|---|
| | Lungs [$Log_{10}(EID_{50}/g)$] | Trachea [$Log_{10}(EID_{50}/ml)$] | Cloaca [$Log_{10}(EID_{50}/ml)$] |
| 6tagWF10:2ckH7N2 | 4.0 ± 1.0 | 2.9 ± 0.6 | 2.4 ± 0.5 |
| 6attWF10:2ckH7N2 | BLD[b] | 2.7 ± 0.3 | 1.0[c] |

[a]Three 3-week old White Leghorn chickens were inoculated intraocularly, intranasally, orally, intratracheally and cloacally with 5 × 10⁶ $EID_{50}$ dose of virus. Three days post infection, the tracheal and cloacal swabs were collected, and lung homogenates were prepared. The experiment was repeated once. Values are means ± standard errors for six chickens. The detection limit is 0.7 $log_{10}EID_{50}$/ml.
[b]BLD, below limit of detection.
[c]Two out of six infected chickens positive with 1.0 $Log_{10}EID_{50}$/ml.

weeks post-vaccination, the chickens were challenged with 100 $CID_{50}$ of the low pathogenic Ck/04 (H7N2) virus by the intranasal route. Eight unvaccinated chickens were used as positive controls to determine the replication efficiency of the challenge virus. The protective efficacy of the vaccine is shown as the reduction of virus shedding in both trachea and cloaca compared to unvaccinated controls. Both tracheal and cloacal swabs were collected at days 3, 5, and 7 post-challenge to determine the amount of virus shedding. The chickens vaccinated with equal or more than $5×10^3$ $EID_{50}$ of 6attWF10:2ckH7N2 virus were protected from virus re-infection. Two birds in the group vaccinated with 500 $EID_{50}$, which seroconverted at 14 days post-vaccination, were also fully protected from virus infection. Our results indicate that a relatively small amount of vaccine virus inoculum ($\geq 5×10^3$ $EID_{50}$) was sufficient to provide adequate protection against challenge with a low pathogenic avian influenza virus strain. In contrast, the 8 unvaccinated control chickens shed a substantial amount of virus after challenge (Table 4).

Example 4

In Ovo Vaccination Protects Chicken from Challenge with a Highly Pathogenic Avian H5N1 Virus In order to better establish the efficacy of our live attenuated virus we performed challenge studies using a HPAI H5N1 virus, A/VN/1203/04. In addition, we wanted to establish whether in ovo vaccination of 18-day-old chicken embryos with or without boost vaccination could be a potential viable alternative to protect chickens against challenge with the HPAI H5N1 virus. We initially generated the 6attWF10:2 H5ΔN1 virus, which contains the HA and NA genes of A/VN/1203/04 vaccine strain (6PR8:2 H5ΔN1) in which the multiple basic amino acids of the HA cleavage site have been removed (as provided by CDC). The internal genes of the 6attWF10:2 H5ΔN1 virus correspond to the WF10 att backbone (ts and HA tag). Replication and transmission studies using the 6attWF10:2 H5ΔN1 virus were carried out on 2

TABLE 4

Dose-dependent H7N2 att vaccination study in chickens challenged with low pathogenic avian influenza Ck/04 (H7N2) [a]

| | Post-vaccination | Post-challenge | | | | | | |
|---|---|---|---|---|---|---|---|---|
| Vaccine dose ($EID_{50}$) | HI titer 14 days p.v. (GMT) | Virus isolation from the swabs: shedding/Total [$Log_{10}(EID_{50}/mL) ± STD$] [b] | | | | | | HI titer 14 days p.c. (GMT) |
| | | Tracheal | | | Cloacal | | | |
| | | 3 DPI | 5 DPI | 7 DPI | 3 DPI | 5 DPI | 7 DPI | |
| $5 × 10^1$ | 0/3 | 3/3 (4.2 ± 0.8) | 3/3 | 2/3 | 0/3 | 0/3 | 0/3 | 3/3 (47) |
| $5 × 10^2$ | 2/3 (25) | 1/3 (3.2) | 1/3 | 1/3 | 0/3 | 0/3 | 0/3 | 3/3 (80) |
| $5 × 10^3$ | 3/3 (53) | 0/3 | 0/3 | 0/3 | 0/3 | 0/3 | 0/3 | 3/3 (213) |
| $5 × 10^4$ | 3/3 (66) | 0/3 | 0/3 | 0/3 | 0/3 | 0/3 | 0/3 | 3/3 (106) |
| $5 × 10^5$ | 3/3 (53) | 0/3 | 0/3 | 0/3 | 0/3 | 0/3 | 0/3 | 3/3 (186) |
| $1 × 10^6$ | 8/8 (46) | 0/8 | 0/8 | 0/8 | 0/8 | 0/8 | 0/8 | 8/8 (65) |
| 0 | 0/8 | 8/8 (4.6 ± 1.1) | 8/8 | 8/8 | 0/8 | 3/8 (3.5 ± 0.6) | 3/8 | 8/8 (64) |

[a] Six groups of 2 week-old chickens were immunized through intraocular, intranasal, oral and intratracheal inoculation with the 6attWF10:2ckH7N2 vaccine strain at doses of either 50, 500, $5 × 10^3$, $5 × 10^4$, $5 × 10^5$, and $1 × 10^6$ $EID_{50}$ in 0.5 ml of diluent. Group of 8 chickens vaccinated only with PBS served as challenge control for virus shedding. Two weeks after vaccination, chickens were challenged by intranasal inoculation with $5 × 10^5$ $EID_{50}$/0.2 ml of Ck/04 (H7N2). Tracheal and cloacal swabs were collected for virus titration every two days for 7 days post-challenge. Sera were collected 2 weeks after vaccination and 2 weeks after challenge. Sera were tested for antibodies to the HA by hemagglutination inhibition test. Data are shown as the ratio of the number of animals affected to the total number of animals per group. GMT, geometric mean reciprocal end point titer; p.v. post-vaccination, p.c. post-challenge.
[b] Mean virus titers are represented as $log_{10}$ $EID_{50}$/ml (±standard deviation). The detection limit is 0.7 $log_{10}EID_{50}$/ml.

week-old White Leghorn chickens. Once again we found that the virus is highly attenuated: only trace amount of virus shedding were detected at 3 days post-infection through the trachea, with no virus shedding detected in lung or cloaca; the virus was not be able to transmit to the direct contact chickens (data not shown).

Based on our previous studies with the H7 vaccine virus, we chose two doses of the 6attWF10:2 H5ΔN1 virus to immunize the chickens: A high dose ($10^6 EID_{50}$) or low dose ($10^4 EID_{50}$). In ovo administration of the 6attWF10:2 H5ΔN1 live-attenuated vaccine virus was performed as described in the materials and methods. Thirty eggs per group were inoculated with either a high or low dose of the vaccine virus or with PBS as mock vaccine control. Hatchability of the high dose group was 85% whereas those of the low dose or PBS were 90%. Ten tracheal and cloacal swabs were taken from each of the two in ovo vaccinated groups at 3 days post-vaccination (1 day post-hatching). Only trace amounts of virus shedding were detected from the tracheal swabs of 3 out of 10 chickens in the low dose group and 4 out of 10 chickens in the high dose group (Table 5). No virus shedding was detected from cloacal swabs in any of the groups. Subsequently a subset (8/group) of the in ovo vaccinated birds received a second boost vaccination at 2 weeks post-hatching. The boost vaccination consisted of either a low dose or a high dose of vaccine virus, which were administered to the low dose and high dose in ovo vaccinated groups, respectively. Analysis of vaccine virus shedding in birds that received the second boost showed traces of virus in only one out 8 chickens in the low dose group and none in the high dose group. In addition, a group of 8, 2 week-old naïve chickens received a high dose of the vaccine with evidence of low virus shedding in only 2 of the chickens. At 4 weeks of age, blood samples were collected from the chickens in the different vaccination groups to determine serum HI titers. Subsequently, the chickens were challenged intranasally with $10^5 EID_{50}$ of the A/VN/1203/04 H5N1 HPAI virus, which is equivalent to 200 chicken lethal dose 50 ($CLD_{50}$). As shown in table 5, HI titers at 4 weeks of age were observed in 6/10 chickens that were vaccinated in ovo with either the high dose or low dose of virus. The chickens that received a second boost of the vaccine at the high dose showed HI titers in 8/8 birds, whereas only 4/8 birds that received a second boost at the low dose showed HI titers. In all cases HI titers were modest, although clearly discernible. Survival after challenge with the HPAI H5N1 virus was observed in all vaccine groups with different efficiencies: 6/10 and 7/10 chickens that received a single in ovo high dose or low dose of vaccine virus, respectively, survived the challenge, whereas 16/16 chickens that received the boost vaccination survived the challenge. Chickens that received a single high dose of the vaccine at 2 weeks post-hatch were also protected although 3/8 chickens died after challenge. In comparison, none of the unvaccinated chickens survived after challenge and the median time to death (MDT) was 1.6 days. Birds that received a single in ovo vaccine dose and did not survive the challenge had a MDT between 2.75 to 3 days, whereas those that were vaccinated at 2 weeks post-hatch and did not survive the challenge had a MDT of 6 days. Interestingly, two other groups of chickens (8/group) that were vaccinated in ovo with a single high dose of the vaccine virus and that were subsequently challenged with the HPAI H5N1 at either 9 weeks or 12 weeks of age showed 100% protection against challenge with no signs of disease (3 times more challenge virus was used in these groups in order to compensate for differences in body weight compared to the 4 week-old birds). Only birds that died from the infection showed signs of disease, none of the survivors (vaccinated) showed overt signs of disease. With respect to virus shedding, vaccinated birds showed between 2 to >4 $log_{10} EID_{50}$ reduction in virus titers compared to unvaccinated birds, in samples taken from tracheal swabs. The effect on reduction of virus shedding was more evident using samples obtained from the cloaca: Only the two 4 week-old groups that received a single dose of the vaccine in ovo showed approximately a 2 $log_{10} EID_{50}$/ml reduction in virus titers, whereas the other vaccinated groups showed no evidence of cloacal virus shedding. It is worth mentioning that no detectable virus shedding was found in both tracheal and cloacal swabs in the high dose prime-boost group. Increased HI antibody titers from surviving birds at 14 days post-challenge suggested that all birds in the vaccine groups did actually respond to the challenge virus.

TABLE 5

Protection efficacy of the live attenuated vaccine against highly pathogenic A/VN/1203/04 (H5N1) challenge in chickens[a]

| Vaccine groups | Virus isolations in trachea at 3 days p.v. ($Log_{10}EID_{50}$/ml)[b,c] | Age (in weeks) at time of challenge | HI serology before challenge (GMT) | Virus isolations at 2 days p.c. ($Log_{10}EID_{50}$/ml)[c] | | Mortality (MDT)[e] | HI serology 14 days p.c. (GMT)[f] |
|---|---|---|---|---|---|---|---|
| | | | | Tracheal | Cloacal | | |
| Control | NA | 4 | 0/10 | 10/10 (6.0 ± 1.0) | 10/10 (6.0 ± 0.7) | 10/10 (1.6) | NA |
| In ovo $10^6$ 1x[a] | 4/10 (1.9 ± 0.3) | 4 | 6/10 (15) | 6/10 (3.5 ± 1.4) | 4/10 (4.3 ± 1.7) | 4/10 (2.75) | 6/6 (45) |
| In ovo $10^4$ 1x | 3/10 (0.7) | 4 | 6/10 (12) | 5/10 (3.0 ± 1.8) | 3/10 (4.0 ± 1.4) | 3/10 (3.0) | 7/7 (108) |
| In ovo $10^6$ 2x | 0/8[d] | 4 | 8/8 (10) | 0/8 | 0/8 | 0/8 | 8/8 (47) |
| In ovo $10^4$ 2x | 1/8 (0.7)[d] | 4 | 4/8 (15) | 4/8 (2.2 ± 0.4) | 0/8 | 0/8 | 8/8 (128) |
| Post-hatch $10^6$ 1x | 2/8 (1.2 ± 0.7) | 4 | 2/8 (10) | 5/8 (1.6 ± 0.8) | 0/8 | 3/8 (6.0) | 5/5 (180) |
| Control | NA | 9 | 0/8 | 8/8 (6.1 ± 0.9) | 8/8 (5.6 ± 0.7) | 8/8 (1.6) | NA |
| In ovo $10^6$ 1x | ND | 9 | 8/8 (18) | 4/8 (1.8 ± 0.8) | 0/8 | 0/8 | 8/8 (255) |
| Control | NA | 12 | 0/8 | 8/8 (5.5 ± 0.5) | 8/8 (5.2 ± 0.5) | 8/8 (1.6) | NA |

TABLE 5-continued

Protection efficacy of the live attenuated vaccine against highly pathogenic A/VN/1203/04 (H5N1) challenge in chickens[a]

| Vaccine groups | Virus isolations in trachea at 3 days p.v. ($Log_{10}EID_{50}$/ml)[b,c] | Age (in weeks) at time of challenge | HI serology before challenge (GMT) | Virus isolations at 2 days p.c. ($Log_{10}EID_{50}$/ml)[c] | | Mortality (MDT)[e] | HI serology 14 days p.c. (GMT)[f] |
|---|---|---|---|---|---|---|---|
| | | | | Tracheal | Cloacal | | |
| In ovo $10^6$ 1x | ND | 12 | 6/8 (10) | 6/8 (1.9 ± 0.7) | 0/8 | 0/8 | 8/8 (840) |

[a]Chickens were vaccinated with $10^6$ $EID_{50}$ or $10^4$ $EID_{50}$ of virus by in ovo administration or at 2 weeks post-hatching. At 4, 9 or 12 weeks of age, the chickens were challenged with A/VN1203/04. Data are shown as the ratio of the number of animals affected to the total number of animals per group; p.v., post-vaccination; p.c., post-challenge; NA, not available; ND, not done; 1x = single vaccination dose; 2x = in ovo vaccination followed by boost vaccination at two-weeks post-hatch.
[b]Virus isolation in tracheal swabs are shown. Virus isolations from cloacal swabs were negative.
[c]Mean virus titers are represented as $log_{10}EID_{50}$/ml (±standard deviation). The detection limit is 0.7 $log_{10}EID_{50}$/ml.
[d]Virus titers after boost vaccination.
[e]MDT, median time to death in days.
[f]GMT, geometric mean reciprocal end point titer.

Our studies indicated that chickens that received a single high dose of the vaccine in ovo were more resistant to the HPAI challenge at 9-12 weeks than at 4-weeks of age. In order to better understand this effect and to determine whether it was related to the kinetics of antibody production, serum samples were randomly collected from eight of the birds on a weekly basis, and the HI antibody titers determined (data not shown). Discernable antibody titers were noticeable in 6 out 8 birds at 3 weeks of age, and reached peak titers when the birds were 6 week-old, slowly decreasing thereafter. Our studies also showed that all the chickens that had discernable HI titers survived the challenge with the HPAI H5N1 virus; however, protection was also observed in some birds that did not show measurable seroconversion. Interestingly, since the 12 week-old chickens exhibited less HI antibody titers than the 4 week-old chickens, survival of older birds may not be necessarily due solely to increased neutralizing antibody titers but to a combined effect of humoral and cellular responses, which were functioning adequately by the time these birds were challenged.

Discussion

In this study, we tested the potential of the att viruses as a live vaccine for poultry in the low and highly pathogenic avian influenza challenge models. Our studies revealed that both the H7 and H5 double mutant att (ts+HA tag) viruses were highly attenuated in chickens. While the att viruses were able to replicate in the upper respiratory tract of birds, no virus or little virus was found in the lungs or cloaca, respectively. No evidence of transmission of the att viruses were observed in chickens, no virus shedding and no seroconversion were observed in the contact birds. An obvious advantage of a potential live attenuated avian influenza vaccine is the possibility of a lower amount of virus/antigen needed in order to provide complete protection compared to an inactivated virus vaccine. In addition, since it is a live virus it is expected to have less variability in terms of protective efficacy from lot to lot as compared to the variations observed in the preparation of inactivated vaccines (which are usually compensated with the type and amount of adjuvant used). In the low pathogenic H7N2 challenge study, our approach appears superior compared to a H7 inactivated vaccine, which contains the equivalent of $10^{7.0}$ $EID_{50}$ of virus per dose, and requires booster vaccination to achieve 100% protection for chickens challenged with the low pathogenic A/Turkey/VA/55/02 (H7N2) virus at dose of $10^5$ $EID_{50}$(Lee et al., 2004, Vaccine 22, 3175-3181). We observed that with a single immunization scheme of the live attenuated vaccine at a dose of $5\times10^3$ $EID_{50}$ in chickens provided full protection against infection with $5\times10^5 EID_{50}$ of the Ck/04 virus. We also performed additional studies in which vaccinated birds were placed in contact with naïve birds challenged with the wild type Ck/04 virus and a naïve uninfected control group. Under these circumstances, no evidence of transmission of the Ck/04 virus to vaccinated birds was observed by either virus isolation or increased seroconversion, whereas the virus was readily transmitted to the naïve control group (not shown).

The 6attWF10:2 H5ΔN1 vaccine virus appears either more attenuated (or less immunogenic than the 6attWF10:2 H7N2 counterpart) since only 2 out of 8 birds showed HI titers when administered at high dose of $10^6$ $EID_{50}$; in fact the 6attWF10:2 H7N2 vaccinated birds showed measurable HI antibody titers even when chickens received a dose of vaccine virus of just $5\times10^3EID_{50}$. Therefore, in order to maximize the humoral response against the H5 virus, we administered the 6attWF10:2 H5ΔN1 to 18-day-old chicken embryo in ovo. Our results show that a single dose of the vaccine in ovo induced protective immunity, which provided 100% protection against HPAI H5N1 virus challenge for chickens between 9 to 12 week-old. Neutralizing antibody titers induced by the vaccine peaked around 6 weeks post-hatching, tempting to speculate that the chickens could be fully protected from 6 weeks old. A boost immunization at 2 weeks post-hatching was required to confer 100% protection to challenge at 4 weeks old. In both of our H7 and H5 vaccination studies, some of the immunized chickens did not show high levels of seroconversion although they were fully protected against challenge. Since our approach utilizes a live attenuated virus, it is plausible that local mucosal immunity and/or cellular-mediated immunity also contribute to the protection.

Coincidentally, it has been shown that a cold-adapted avian pneumovirus vaccine achieved full protection in turkeys showing very low levels of seroconversion (Patnayak et al., 2003, Vaccine 21, 1371-1374).

The generation of a attenuated avian influenza virus was based on the incorporation of is mutations found on the PB1 and PB2 genes of the ca/ts/att influenza A/Ann Arbor/6/60 (H2N2) strain and the cloning of a HA tag in frame with the C-terminus of the PB1 gene. An important distinction between avian and human influenza viruses relates to their optimal temperature of replication. While human influenza A viruses replicate in the upper respiratory tract at a temperature around 33° C., avian viruses tend to replicate in the intestinal tract of aquatic birds at a temperature about 41° C. It is reasonable to speculate that amino acid differences in the internal genes of avian and human influenza viruses are responsible for the optimal temperature of replication. For example, the amino acid position 627 in PB2 has been shown to play a role in host range and virulence. Typical avian influenza viruses encode for glutamic acid at position 627, whereas human influenza viruses and some of the most lethal forms of H5N1 viruses that have crossed to humans encode for a lysine. It has been shown that glutamic acid at position 627 is also a determinant of cold sensitivity of avian influenza viruses; i.e. it prevents them from growing at temperatures below 33° C. (Massin et al., 2001, J. Virol. 75, 5398-5404; Shinya et al., 2004, Virology 320, 258-266; Subbarao et al., 1993, J. Virol. 67, 1761-1764). The avian influenza virus used in this study possesses glutamic acid at position 627 in PB2. Therefore, incorporation of the ts mutations would not necessarily imply the same level of ts phenotype for an avian influenza virus than a human influenza virus. Thus the nonpermissive temperature for the ca/ts/att human virus is around 38° C. in MDCK cells (Jin et al., 2004, supra), whereas for the WF10 virus was 39° C.

Host factors may also play a role in determining the ts phenotype since our studies using cells from mammalian and avian origin showed differences in the ability of our mutant viruses to form plaques and in protein synthesis. For example, the three different mutant viruses (7tsWF10:1malH7, 7tagWF10:1malH7, and 7attWF10:1malH7) exhibited more evident ts phenotypes in mammalian cells than in chicken cells. This observation correlates with the observation that viruses containing the WF10ts backbone are not attenuated in chickens; however, they are substantially attenuated in mice (Hossain et al., unpublished). Previous studies showed that the heat-shock protein of 70 kDa (HSP70) expressed at 41° C. in MDCK cells inhibited the binding of the viral M1 protein to vRNPs and their subsequent nuclear export (Hirayama et al., 2004, J. Virol. 78, 1263-1270). The different growth characteristics of the WF10 in MDCK and CEK cells may reflect distinct interaction patterns between viral proteins and host factors induced in different host cells at higher temperatures.

The incorporation of a HA tag in frame with the C-terminus of PB1 provided a genetic marker to differentiate the vaccine strain from the field isolates (using real-time RT-PCR, the HA tag sequence was detected in the swab samples from the vaccinated birds but not in the birds infected by the field isolates, data not shown). The introduction of unrelated sequences into the PB1 gene did not affect the viruses' viability. This is partially due to the fact that the noncoding regions and the last 12 nucleotides of both the 5' and 3' coding region of the PB1 vRNA were not altered, which have recently been shown to be sufficient for efficient incorporation of the PB1 vRNAs (Muramoto et al., 2006, J. Virol., 80, 2318-2325). It is interesting to note that introduction of HA tag alone has little attenuating effect by itself, but acts synergistically with the four ts mutations in PB1 and PB2. Our results indicated that the all the ts mutations contribute the ts phenotype of HA tagged viruses, among these ts mutations, 391E and 661T in PB1 are sufficient to provide ts phenotype as the same level as the 7attWF10:1malH7 virus. The influenza virus RNA polymerase is a heterotrimer comprising the PB1, PB2 and PA subunits, PB1 functions as the RNA polymerase catalytic subunit (Biswas and Nayak, 1994, J. Virol. 68, 1819-1826). The N-terminal region of PB1 interacts with the C-terminal region of PA, while the C-terminal region of PB1 interacts with the N-terminal of PB2 subunit (Gonzalez et al., 1996, Nucleic Acids Res. 24, 4456-4463; Perez and Donis, 1995, J. Virol. 69, 6932-6939; Perez et al., 2003 Avian Dis. 47, 1114-1117). Further studies are needed to determine whether the incorporation of the HA tag at the C-terminus of PB1 harboring the ts mutations affects the interaction with PB2, which may be potentially disrupted at higher temperatures. To determine whether replication of the double mutant virus in birds would result in loss of either the ts loci, the HA tag modification, or both, RT-PCR and sequencing were performed on viruses recovered from the vaccinated birds. Results from tracheal samples collected at 5 days post-vaccination from all the vaccinated birds revealed the expected integrity of the ts loci and/or HA tag mutations suggesting that the host did not induce genetic alterations in these viruses (not shown). No changes in the in vitro phenotype of the mutant viruses were observed, which are consistent with the sequence analysis. Likewise, serial passage in eggs (10 times) of the att virus did not result in mutations at either the ts loci or the HA tag modification, and the virus maintained its expected ts restricted phenotype in vitro. We also took advantage of the HA tag in the att virus to discriminate the vaccine virus from the wild type virus by real-time RT-RCR (data not shown) using the specific set of primers shown in FIG. 1. Therefore, these results suggest that the att virus is genetically stable and that no reverent compensatory mutations have emerged.

Taken together, our results suggest that live attenuated avian influenza viruses could have potential as safe live vaccines and applied for mass vaccination using the in ovo route. The use of in ovo vaccination would also alleviate concerns regarding potential reassortment with other viral strains since it is commonly accepted that wild type avian influenza viruses are not usually found in commercial chicken eggs. However, since reassortment is common among influenza A viruses, particularly in avian species, additional studies are required to evaluate the reassortment potential of our live attenuated virus with other influenza A viruses. Strategies that prevent the reassortment of the vaccine virus with other influenza viruses, particularly of the HA gene, will facilitate the use of live influenza vaccines in poultry. Further studies are also needed to test other delivery routes for mass vaccination purposes; i.e. aspersion, through drinking water, etc.

Example 5

In Vitro Characterization of Recombinant Viruses Carrying the Internal Genes of the Genetically Modified Influenza A/Guinea Fowl/Hong Kong/WF10/99 (H9N2)

To further characterize the biological properties of attenuated viruses using the WF10 backbone and to determine their potential as universal vaccine donors, we created additional recombinant viruses and tested them in vitro. We rescued three recombinant viruses, called 6WF10:2 H1N1, 6WF10ts: 2H1N1 and 6WF10att:2H1N1. The 6WF10:2 H1N1 virus contains the internal genes of the WF10 virus and the HA and NA genes of the influenza A/WSN/33 (H1N1) virus. The genetic background of the 6WF10ts:2H1N1 virus is the same as the 6WF10:2 H1N1 virus, except that the PB2 and PB1 genes carry the (ca/ts/att) MDV-A mutations. The 6WF10att: 2H1N1 virus carried the ca/ts/att loci and HA tag modification.

We analyzed the growth characteristics of the recombinant viruses at different temperatures in MDCK cells. The recombinant viruses grew as efficient as the wild type in eggs incubated at 35° C. with titers $\geq 7.0$ $\log_{10}$ PFU/ml (Table 6). Plaque formation in MDCK cells for the 6WF10ts:2H1N1 and 6WF10att:2H1N1 viruses was impaired at 37° C. compared to the 6WF10:2 H1N1 virus, which is consistent with the presence of is mutations in their respective backbones. The 6WF10att:2H1N1 and 6WF10ts:2H1N1 viruses produced relatively larger plaques and grew better at 32° C. than at 37° C. or 38.5° C. (Table 6). As expected, the 6WF10:2 H1N1 virus did not show significant reduction in plaque numbers at 37° C. and only a slight 0.5 $\log_{10}$ reduction at 38.5° C. In contrast, plaque formation by the 6WF10ts: 2H1N1 virus was reduced by 0.6 $\log_{10}$ at 37° C. and 3.4 $\log_{10}$ at 38.5° C., respectively, compared to 32° C. The 6WF10att: 2H1N1 double mutant virus had reduced plaque numbers by 1.0 $\log_{10}$ at 37° C. and was unable to produce plaques at 38.5° C., which is consistent with our previous observations. These studies suggest that the is phenotype in our WF10 backbone will be manifested regardless of its surface genes.

TABLE 6

Reduction of recombinant virus titers at the indicated temperatures compared to the permissive temperature[a]

| Viruses | Plaque reduction ($\log_{10}$ PFU/ml) | | Stock virus titer[b] ($\log_{10}$ PFU/ml) |
|---|---|---|---|
| | 37° C. | 38.5° C. | |
| 6WF10att:2H1N1 | 1.0 | NP | 7.3 |
| 6WF10ts:2H1N1 | 0.6 | 3.4 | 7.6 |
| 6WF10:2H1N1 | −0.1 | 0.5 | 7.4 |
| WSN | 0.3 | 1.2 | 7.3 |

[a]Permissive temperature is 32° C.
[b]Viruses were grown for 48 h in the allantoic cavity of 10-day old embryonated chicken eggs. The amount of virus in the allantoic fluid was determined by plaque assay on MDCK cells at 32° C. NP, no plaques detected. Results represent the average of two independent experiments.

Example 6

Genetically Modified WF10att Viruses with H1N1 Surface Genes are Attenuated in Mice Mice were inoculated with different doses of the WSN wild type, 6WF10:2 H1N1, 6WF10ts:2H1N1, or 6WF10att: 2H1N1 viruses. Severe clinical symptoms were observed in mice infected with WSN. Four out of 4 mice succumbed to the infection within 8 days when inoculated with either $10^6$ or $10^5$ PFU of virus (Table 7). Likewise, mice infected with the 6WF10:2 H1N1 virus showed severe signs of disease and half of them died (2 out of 4) when inoculated with $10^6$ PFU of virus (Table 7). Noticeable reduction in body weight was also observed when mice were inoculated with $10^5$ PFU of the 6WF10:2 H1N1 virus (data not shown). In contrast, mice infected with the 6WF10ts:2H1N1 or the 6WF10att:2H1N1 virus exhibited no clinical signs of influenza infection and none of them died (data not shown). These results indicate that the 6WF10ts:2H1N1 and 6WF10att:2H1N1 viruses are attenuated in mice.

Next, we checked the replication of recombinant viruses in mouse lungs. As shown in Table 8, the 6WF10ts:2H1N1 virus replicated very poorly in mouse lungs. The growth of the 6WF10ts:2H1N1 virus in mouse lungs is about 1.4 and 3.8 $\log_{10}$ lower than for the 6WF10:2 H1N1 or WSN virus. This difference was higher when mice were inoculated with a lower dose of virus. Furthermore, the double mutant 6WF10att:2H1N1 virus was even more attenuated in

TABLE 7

Survival of mice following infection with recombinant viruses generated by reverse genetics

| Virus | Infection dose[a, b] | Survival[c] (no. of survivors/no tested) |
|---|---|---|
| A/WSN/33 (H1N1) | $10^{6a}$ | 0/4 |
| | $10^5$ | 0/4 |
| 6WF10:2H1N1 | $10^6$ | 2/4 |
| 6WF10att:2H1N1 | $10^6$ | 4/4 |
| A/Vietnam/1203/04 (H5N1) | $10^{6b}$ | 0/4 |
| 6WF10:2H5N1 | $10^6$ | 0/4 |
| 6WF10att:2H5N1 | $10^6$ | 2/4 |
| 6WF10att:2ΔH5N1 | $10^6$ | 4/4 |
| 6WF10att:2H7N2 | $10^6$ | 4/4 |

[a] Mice were infected with viruses at the indicated doses calculated in PFU (A/WSN/33, 6WF10:2H1N1 and 6WF10att:2H1N1) or
[b] $EID_{50}$ (A/Vietnam/1203/04, 6WF10:2H5N1, 6WF10att:2H5N1, 6WF10att:2ΔH5N1, 6WF10att:2H9N2 and 6WF10att:2H7N2).
[c] Survival of mice monitored for 14 dpi.

mice than the 6WF10ts:2H1N1 virus (Table 8). Thus, the growth of the 6WF10att:2H1N1 virus is highly restricted in mice and is consistent with our in vitro plaque reduction assays.

TABLE 8

Replication of recombinant vaccine viruses in mouse lungs at 3 days post-infection

| | Infectious virus dose used ($PFU^a$ or $EID_{50}^b$) | | | |
|---|---|---|---|---|
| | $10^6$ | $10^5$ | $10^4$ | $10^3$ |
| Virus | Titers in PFU/lung[a] or $EID_{50}$/lung[b] | | | |
| WSN | — | 7.1 ± 0.1[a] | 6.8 ± 0.1[a] | 5.5 ± 0.2[a] |
| 6WF10:2H1N1 | — | 4.7 ± 0.1[a] | 4.2 ± 0.3[a] | 3.0 ± 0.2[a] |
| 6WF10ts:2H1N1 | — | 3.3 ± 0.3[a] | 2.2 ± 0.2[a] | BLD[a] |
| 6WF10att:2H1N1 | BLD[a] | BLD[a] | — | — |
| 6WF10att:2ΔH5N1 | BLD[b] | — | — | — |
| 6WF10att:2H7N2 | 2.9 ± 0.8[b] | — | — | — |

[a]Mice were inoculated intranasally with viruses at the indicated dose. At 3 days post-infection, lungs were collected and homogenized for virus titration. Data are the average of virus titers from 4 mice in each group. —, not tested; ND, not detected Example 8

Attenuation in mice of WF10att Viruses in the Context of H5N1 and H7N2 Subtypes

The attenuated phenotype of WF10 recombinant viruses carrying the HA and NA genes of a HPAI H5N1 virus, its LPAI version with the polybasic region of the H5 HA removed (ΔH5N1), and H7N2 subtypes was evaluated in mice (Table 7). Mice inoculated with the 6WF10:2 H5N1 strain, which resembles a wild type HPAI H5N1 virus, showed severe clinical symptoms (Data not shown) and 4 out of 4 mice succumbed to the infection within 10 days (data not shown). Interestingly, mice infected with the 6WF10att: 2H5N1 virus—carrying the att WF10 virus backbone and the wild type HPAI H5N1 surface genes—showed less severe outcome of disease. Although 2 out of 4 mice died, the att WF10 was noticeably less virulent than the 6WF10:2 H5N1 or the HPAI H5N1 wt virus. This observation was further confirmed by $MLD_{50}$ assays which required $10^6$ EID50 of the 6WF10att:2H5N1 virus compared to $<10^2$ $EID_{50}$ for the 6WF10:2 H5N1 (the exact lower limit was not tested) or 1 $EID_{50}$ for the HPAI H5N1 virus (data not shown). These results highlight the attenuated nature of the WF10 att backbone even in the context of HPAI H5N1 surface genes. As expected, mice infected with either the 6WF10att:2ΔH5N1 or the 6WF10att:2H7N2 viruses exhibited no clinical signs of influenza infection and none of them died. The 6WF10att: 2ΔH5N1 virus was not detected in the lungs; however, the 6WF10att:2H7N2 virus was detected in the lungs 3 dpi (Table 8). The limited, although clearly discernible, replication of the 6WF10att:2H7N2 virus in mouse lungs contrasted with the absence of the virus in chickens and quail lungs as described previously (Song et al., 2007, J. Virol. 81, 9238-9248). We must note that the 6WF10att:2H7N2 obtained from mouse lungs was not a non attenuated reverent strain. For reasons that are beyond the scope of this report, the 6WF10att:2H7N2 virus showed better replication in mouse lungs than the 6WF10att:2H1N1 or 6WF10att:2ΔH5N1 viruses (Table 8). Nevertheless, these results indicate that the WF10 att backbone is attenuated in mice despite which surface proteins are present.

Example 9

The WF10att Backbone Provides Protection in Mice Against Homologous Challenge with Lethal H1N1 or H5N1 Subtypes In order to determine the protective efficacy of the 6WF10att backbone for mice against the WSN virus, we immunized mice intranasally with $10^4$, $10^5$ or $10^6$ PFU of the 6WF10att:2H1N1 virus. At 21 dpi, mice were challenged with a lethal dose of the virulent WSN virus. The mice immunized with the 6WF10att:2H1N1 virus survived the challenge with no signs of disease, although a significant decrease in body weight was observed in the group immunized with the lowest vaccine dose (data not shown). In contrast, the mock-immunized group developed severe pneumonia, showed drastic body weight loss and eventually died within 8 dpi (data not shown). More importantly, mice vaccinated with $10^6$ PFU of the 6WF10att:2H1N1 virus showed significant reduction of the challenge virus from lungs by 3 dpi in contrast to the mock-vaccinated mice (Table 9). These data suggest that at doses that showed either very limited or undetectable replication in the mouse lung, the 6WF10att:2H1N1 virus was able to induce immune responses that completely protected mice from challenge with the lethal WSN virus.

We next evaluated the protection of the recombinant 6WF10att:2ΔH5N1 against HPAI H5N1 challenge. Our results show that all mice vaccinated with 6WF10att: 2ΔH5N1 were protected against lethal HPAI H5N1 challenge (data not shown). Slight body weight loss (about 10%) was evident between 5 to 8 dpc. All mice gained body weight thereafter without overt signs of disease. In contrast, mock vaccinated mice succumbed to the challenge by day 10 (data not shown). Virus clearance was monitored at days 3 and 6 post-challenge. As shown in Table 9, virus titers within the lungs were significant, although a very slight reduction was observed in mice vaccinated with the 6WF10att:2ΔH5N1 at 6 dpc with a reduction of 0.6 $log_{10}$ EID50. Since a significant amount of virus was detected in the immunized mice at 3 and 6 days post-challenge despite complete protection against the HPAI H5N1 virus, we wanted to test whether a boost immunization would result in a better response and faster virus clearance (Table 9 and data not shown). Our results suggest that boost immunization improves the overall response to HPAI H5N1 challenge. No significant body weight loss was detected in the boosted mice while substantial reduction in challenged virus was seen in the boost group 6 dpc, only 2.3 $log_{10}$ $EID_{50}$ of virus was present compared with single immunization where 4.9 $log_{10}$ $EID_{50}$ of virus was present. These results suggest that the single dose of the 6WF10att backbone can protect mice against homologous virus challenge, but a boost leads to faster virus clearance.

Example 10

The 6WF10att Backbone Provides Protection in Mice Against Heterologous Challenge In order to understand whether intranasal immunization of recombinant viruses induce cross protective immunity against H1N1 or H5N1 viruses, groups of 4 or 10 mice were immunized with a heterologous subtype, 6WF10att:2H7N2 virus (Song et al., 2007, supra). Mice immunized with a single dose of 6WF10att:2H7N2 survived the lethal challenge with both the WSN virus and HPAI H5N1 (data not shown). Mice immunized with the 6WF10att:2H7N2 virus showed some body-weight loss (about 15% between days 4 and 6) although they all survived the challenge. These results suggest that the 6WF10att backbone is capable of providing cross-protective immunity against two different lethal virus challenges. Inter-

TABLE 9

Clearance of challenge virus in mice immunized with recombinant vaccine viruses.

| Immunized with | Immunization dose $log_{10}$ (PFU or EID50)/mouse) | Challenged with 20 MLD50 of[a] | Challenge virus titer in $log_{10}$ ($PFU^a$ or $TCID_{50}^b$/lung at 3 dpc | Challenge virus titer in $log_{10}$ $TCID_{50}$/lung at 6 dpc |
|---|---|---|---|---|
| PBS | | WSN | $7.3 \pm 0.1^a$ | — |
| WSN | $10^3$ | WSN | $BLD^a$ | — |
| 6WF10att:2H1N1 | $10^6$ | WSN | $BLD^a$ | — |
| 6WF10att:2H1N1 | $10^5$ | WSN | $2.8 \pm 0.9^a$ | — |
| PBS | | HPAI H5N1 | $5.7 \pm 0.3^b$ | $7.1 \pm 0.3$ |
| 6WF10att:2ΔH5N1 | $10^6$ | HPAI H5N1 | $5.5 \pm 0.4^b$ | $4.9 \pm 0.1$ |
| 6WF10att:2ΔH5N1 + boost | $10^6$ | HPAI H5N1 | $6.8 \pm 0.2^b$ | $2.3 \pm 0.1$ |
| 6WF10att:2H7N2 | $10^6$ | HPAI H5N1 | $5.0 \pm 0.3^b$ | $5.1 \pm 0.3$ |
| 6WF10att:2H7N2 + boost | $10^6$ | HPAI H5N1 | $5.8 \pm 0.2^b$ | $5.8 \pm 0.8$ |

[a]immunized mice were challenged with $10^5$ PFU of WSN virus or 20 $EID_{50}$ of HPAI H5N1 (equivalent to 20 $MLD_{50}$).
3 or 6 days later, lungs were collected and homogenized; virus titers were assayed by plaque assay or $TCID_{50}$ in MDCK cells. Data indicates the average lung virus titer from 3 mice/group. BLD, below limit of detection. —, not tested.

estingly, significant virus titers were found at 3 and 6 dpc in lungs of mice challenged with the HPAI H5N1 virus (Table 9). We investigated whether improved clearance of the challenged virus could be achieved following a boost vaccination regime (Table 0 and data not shown). Mice that received two doses of the 6WF10att:2H7N2 virus showed minimal weight loss, displayed no disease signs, and were completely protected from challenge with HPAI H5N1. However, single dose and boost immunization groups had similar levels of challenge HPAI H5N1 virus 3 or 6 dpc (data not shown and Table 9). We must note that heterologous protection was not necessarily due to the 6WF10att:2H7N2 virus' ability to replicate in mouse lungs. Using another WF10 att subtype virus, the 6WF10att:2H9N2 virus, which did not replicate in mouse lungs, we achieved similar levels of cross-protection (not shown). These results suggest that protection by the 6WF10att:2H7N2 virus is likely provided by cell-mediated mechanisms that do not prevent initial replication of the HPAI H5N1 virus. Thus, the 6WF10att backbone provides protection in mice against heterologous challenge with either WSN or HPAI H5N1 viruses, although it does not prevent virus replication at early stages of infection.

Example 11

Significant Variations in the Ability of Recombinant WF10att Viruses to Induce Neutralizing Antibody Responses To evaluate the immune responses induced by the WF10 att viruses that protected mice against lethal challenge with WSN and HPAI H5N1, we determined the levels of neutralizing antibody in the sera of immunized mice using microneutralization assays. As shown in Table 10, discernible and adequate neutralizing responses were observed in mice immunized with the 6WF10att:2H1N1 virus, which is similar to those obtained using either the 6WF10:2 H1N1 or WSN viruses (not shown). Lower neutralizing antibody titers were observed in the pooled sera of the 4 surviving mice immunized with a single dose of 6WF10att:2H7N2 virus against its homologous virus; however, after boosting an increased neutralizing antibody titer was clearly observed (Table 10). As expected, the 6WF10att:2H7N2

TABLE 10

Microneutralization (MN) antibody titers in mouse sera against homologous and heterologous viruses.

| Immunized with | Immunization dose[a] | MN titers against homologous virus[b,c] | MN titers against WSN | MN titers against H5N1 |
|---|---|---|---|---|
| PBS | | <10 | <10 | <10 |
| 6WF10att:2H1N1 | 10[6] | 160 | 160 | <10 |
| 6WF10att:2H1N1 | 10[5] | 80 | 80 | <10 |
| 6WF10att:2ΔH5N1 | 10[6] | <10 | <10 | <10 |
| 6WF10att:2ΔH5N1 + boost | 10[6] | <10 | <10 | <10 |
| 6WF10att:2H7N2 | 10[6] | 40 | <10 | <10 |
| 6WF10att:2H7N2 + boost | 10[6] | 160 | <10 | <10 |

[a]Immunization dose in $\log_{10}$ PFU/mouse for 6WF10att:2H1N1 and $\log_{10}$ EID$_{50}$/mouse for other viruses.
[b]Sera were collected at 21 days post-immunized. Data represents pooled sera from 4 mice/group.
[c]Microneutralization assays performed using homologous viruses:A/WSN/33 (H1N1), A/Vietnam/1203/04 (ΔH5N1),and A/chicken/Delaware/VIVA/04 (H7N2).

virus showed no cross reactive antibodies that could neutralize the heterologous WSN or H5N1 viruses.

This observation strongly suggest that cell-mediated mechanisms provide protection by the 6WF10att:2H7N2 virus against the WSN or HPAI H5N1 viruses (data not shown or Table 10). Interestingly, the mice vaccinated with the 6WF10att:2ΔH5N1 showed no discernible neutralizing antibody reaction even after boost immunization. These results were consistent with previous observations (Lu et al., 2006, Vaccine 25, 6588-6593). Neutralizing antibody titers against the HPAI H5N1 virus were undetectable even after boost immunization, despite 100% survival in challenge studies (Lu et al., 2006, supra).

Discussion

Recent studies indicated that transferring the ts amino acid signature of the MDV-A virus into different human influenza strains resulted in temperature sensitivity in vitro and attenuation in ferrets (Jin et al., 2004, supra). Because of the transferable nature of the ts mutations of the MDV-A virus, we sought to determine whether such mutations would impart a similar phenotype to an avian influenza virus. For that purpose we chose a virus that has demonstrated broad host range in order to generate an attenuated virus backbone that could be used for the development of vaccines for multiple animal species, i.e. from poultry to humans. We chose the internal genes of the avian influenza A/Guinea fowl/Hong Kong/WF10/99 (H9N2) virus which replicates and transmits efficiently in birds, causes respiratory disease in mice without adaptation, and replicates efficiently in ferrets (Wan et al, unpublished data) (Choi et al., 2004, J. Virol. 78, 8609-8614). We successfully generated attenuated H1N1, H5N1, and H7N2 reassortant viruses with the internal genes from the att WF10 virus. Incorporation of the is loci of the MDV-A and an HA tag in the PB1 gene of WF10 resulted in a virus that is highly attenuated in mice, yet produced a good protective response in mice challenge with lethal WSN or HPAI H5N1 viruses.

There are obvious limitations in the preparation of influenza vaccine stocks for pandemic preparedness, which are inherent to the rapid mutability of the virus. Thus, it is not possible to predict whether the antigenic make up of the vaccine seed stock would confer protective immunity against the pandemic strain. Meanwhile, the world is experiencing a pandemic of influenza in birds caused by an H5N1 virus in which multiple domestic and wild avian species are involved (Webster et al., 2007, Avian Dis. 51, 269-272). Although this H5N1 virus has been restricted to Eurasia and some countries in Africa, there is a latent risk that this virus may spread worldwide. The H5N1 virus has also shown an unusual expanded host range, i.e. not only birds and humans have been infected and succumbed to the infection but also feline species, otherwise regarded as resistant to influenza, have experienced a similar fate. In fact, little is known about the extent of the host range of the H5N1 virus in nature. Culling and quarantine complemented with the use of vaccines is being implemented to control the spread of the H5N1 in domestic poultry and to minimize the risk of human exposure (Capua & Alexander, 2002, Acta Trop. 83, 1-6; 2004; Capua & Marangon, 2004, Vaccine 22, 4137-4138). Approved vaccines for poultry rely on inactivated vaccines or a fowl-pox recombinant virus (Capua et al., 2003, Avian Pathol. 32, 47-55). Parenteral administration of these vaccines limits their use in mass vaccination campaigns. The magnitude of a H5N1 outbreak may be managed or prevented with vaccination strategies performed by aspersion, in ovo, or drinking water in which thousands of birds can be immunized at the same time with little labor costs. A second issue has recently emerged during the preparation of inactivated vaccines, and it is related to the human health risks of personnel exposed to AI viruses whose interspecies potential is poorly defined.

For pandemic preparedness and from a practical point of view, it would be ideal to prepare vaccine seed stocks that can be used in multiple animal species. We have explored this latter possibility and have generated an attenuated avian influenza virus with an extended host range that could be used for the preparation of vaccines for either birds or mammals. The use of a universal backbone would obviate the need for the reformulation of the vaccine specifically designed for use in humans, which would save valuable time since the vaccine itself could be already in use for other animal species. A live attenuated AI vaccine for poultry would be amenable for mass vaccination and would negate the limitations associated with recombinant approaches in terms of prior exposure to the wild type virus. The potential of reassortment of the surface genes of our vaccine virus with a wild type virus would limit its use in domestic birds, although this risk could be greatly minimized by performing in ovo vaccination as we have recently shown (Song et al., 2007, supra). Our approach should also allow the mass vaccination of wild bird species in which the H5N1 virus appears to have gone through cycles of increased virulence, the ecological consequences of which remain to be seen. Thus, our strategy provides an alternative approach for the preparation of vaccines for epidemic and pandemic influenza.

What is claimed is:

1. A live attenuated avian influenza virus comprising a PB2 gene with a substitution at position 265, and a PB1 gene with substitutions at positions 391, 581, and 661, said PB1 gene also comprising a genetic tag wherein said genetic tag in PB1 comprises 8 amino acids derived from the influenza virus H3 HA protein sequence, said genetic tag identified as SEQ ID NO:1.

2. The attenuated avian influenza virus of claim 1 wherein said genetic tag is inserted in frame with the C terminus of PB1.

3. The attenuated avian influenza virus of claim 2 wherein said virus is A/Guinea Fowl/Hong Kong/WF 10/99 (H9N2).

4. The avian influenza virus of claim 2 wherein said virus is chosen from the group consisting of: A/Mallard/Alberta/01 (H7N3), A/chicken/Delaware/VIVA/04 (H7N2), A/VN/1203/04 (H5N1), and A/WSN/33 (H1N1).

5. A recombinant attenuated influenza virus, comprising
(i) an avian influenza virus master backbone comprising internal genes of influenza comprising PB2, PB1, PA, NP, M, and NS segments wherein
said PB2 gene has a substitution at position 265, said PB1 has one or more substitutions at 391, 581, and 661, and a genetic tag, wherein said genetic tag comprises 8 amino acids derived from the influenza virus H3 HA protein sequence said genetic tag identified as SEQ ID NO:1; and (ii) HA and NA genes from another selected influenza virus.

6. The recombinant attenuated influenza virus of claim 5 wherein said said genetic tag is inserted in frame with the C terminus of PB1.

7. The recombinant attenuated influenza virus of claim 6 wherein said PB1 gene is SEQ ID NO:3 and said master backbone is from A/Guinea Fowl/Hong Kong/WF 10/99 (attWF10).

8. The recombinant attenuated influenza virus of claim 7 wherein said HA and NA in (ii) are derived from A/Chicken/Delaware/VIVA/04 (H7N2) producing 6attWF10:2ckH7N2.

9. The recombinant attenuated influenza virus of claim 7 wherein said HA and NA in (ii) are derived from A/Vietnam/1203/04 (H5N1) producing 6attWF10:2H5N1.

10. The recombinant attenuated influenza virus of claim 7 wherein said HA and NA in (ii) derived A/Vietnam/1203/04 further having a multiple basic amino acids of the HA cleavage site removed, producing 6attWF10:2 H5ΔN1.

11. The recombinant attenuated influenza virus of claim 7 wherein said HA and NA in (ii) are derived from A/WSN/33 (H1N1) producing 6attWF10:2H1N1.

12. A method for making the attenuated avian influenza virus of claim 1, said method comprising introducing into said virus PB2 gene a substitution at position 265, and into said virus PB1 gene substitutions at positions 391, 581, and 661, and a genetic tag identified as SEQ ID NO:1.

13. The method of claim 12 wherein said genetic tag is inserted in frame with the C terminus of PB1.

14. A method for making the attenuated influenza virus of claim 8, said method comprising producing reassortant virus comprising (i) internal genes PB2, PB1, PA, NP, M, and NS of an avian influenza virus wherein said PB2 contains substitutions at positions 265, and said PB1 contains one or more substitutions at positions 391, 581, and 661, and a genetic tag identified in SEQ ID NO:1; and (ii) HA and NA genes from said another selected influenza virus.

15. The method of claim 14 wherein said internal PB1 is identified in SEQ ID NO:3.

16. The method of claim 14 wherein said internal genes are from an avian influenza virus.

17. The method of claim 16 wherein said internal genes are from an avian influenza master backbone att WF10.

18. A kit for producing a recombinant attenuated influenza virus of a selected strain, said kit comprising the avian influenza virus master backbone in (i) of claim 5.

19. A method for inducing in a subject an immune response against one or more selected strains of influenza virus comprising administering to said subject a composition comprising an immunologically effective amount of attenuated influenza virus according to claim 5.

20. The method of claim 19 wherein said composition further comprises an adjuvant.

21. The attenuated avian influenza virus of claims 3, wherein said virus is 7attWF10:1malH7.

22. An influenza virus vaccine comprising an attenuated influenza virus according to claim 21.

23. An influenza virus vaccine comprising an attenuated influenza virus according to claim 5.

24. An influenza virus vaccine comprising an attenuated influenza virus according to claim 7.

25. An influenza virus vaccine comprising an attenuated influenza virus according to claim 8.

26. An influenza virus vaccine comprising an attenuated influenza virus according to claim 9.

27. An influenza virus vaccine comprising an attenuated influenza virus according to claim 10.

28. An influenza virus vaccine comprising an attenuated influenza virus according to claim 11.

* * * * *

SEQUENCE LISTING

```
<160> NUMBER OF SEQ ID NOS: 7

<210> SEQ ID NO 1
<211> LENGTH: 8
<212> TYPE: PRT
<213> ORGANISM: Artificial sequence
<220> FEATURE:
<223> OTHER INFORMATION: genetic tag

<400> SEQUENCE: 1

Tyr Pro Tyr Asp Val Pro Asp Tyr
 1               5

<210> SEQ ID NO 2
<211> LENGTH: 26
<212> TYPE: PRT
<213> ORGANISM: Artificial sequence
<220> FEATURE:
<223> OTHER INFORMATION: genetic tag hemaglutinin junction

<400> SEQUENCE: 2

Glu Asp Met Tyr Pro Tyr Asp Val Pro Asp
 1               5                  10

Tyr Ala Ser Arg Ile Cys Ser Thr Ile Glu
                15                  20

Glu Leu Arg Arg Gln Lys
                25

<210> SEQ ID NO 3
<211> LENGTH: 2401
<212> TYPE: DNA
<213> ORGANISM: Artificial sequence
<220> FEATURE:
<223> OTHER INFORMATION: PB1 sequence of 7attWF10

<400> SEQUENCE: 3
agcgaaagca ggcaaaccat ttgaatggat gtcaatccga                40
ctttactttt cttaaaagtg ccagcgcaaa atgcaataag                80
taccacattc ccttatactg gagatccccc atatagccat               120
ggaacaggaa caggatacac catggacaca gtcaacagaa               160
cacatcaata ttcagaaaaa gggaggtgga caacaaacac               200
agagaccgga gcacccccaac tcaaccctat tgatggacca              240
ttacctgaag acaatgagcc gagcgggtat gcacaaacag               280
attgtgtatt ggaagcaatg gctttccttg aagaatccca               320
cccagggctc tttgaaaact catgtcttga aacgatggaa               360
```

```
gttgtccagc aaacgagagt ggataagctg acccaaggtc         400
gccagactta tgactggaca ttgaatagaa accagccggc         440
tgcaactgct ttggccaaca ccatagaggt attcagatcg         480
aacggtctaa cagccaatga gtcaggaagg ttaatagatt         520
tcctcaagga cgtaatgaa tcaatggata aggaagaaat          560
ggaaataaca acacatttcc agagaaagag aagagtgagg         600
gacaacatga ccaagaaaat ggtcacacaa agaacaatag         640
ggaagaagaa gcaaaagctg acaaaaaaga gctacctaat         680
aagagcactg acactgaaca caatgacaaa agatgctgaa         720
aggggaaaat tgaaaagacg agcgattgca cacccggaa          760
tgcaaatcag aggattcgtg cactttgtcg aagcactagc         800
aaggagcatc tgtgaaaaac ttgagcaatc tggactaccc         840
gttggaggga atgagaagaa ggctaaattg gcaaatgttg         880
tgagaaagat gatgactaac tcacaagaca cagagctctc         920
ctttacagtt accggagaca acaccaaatg gaatgagaat         960
cagaatcctc gaatatttct agcaatgata acatacatca         1000
caaggaacca acctgaatgg tttagaaatg tcttgagcat         1040
tgcccctata atgttctcaa ataaaatggc gaggttagga         1080
aaaggataca tgttcgagag taagagcatg aagctacgga         1120
cacaaatacc agcagaaatg cttgcaaaca ttgatttgaa         1160
atacttcaac gaatcgacga gaaagaaaat tgaggaaata         1200
agacctctac taatagaggg cacagcctca ttgagtccag         1240
ggatgatgat gggcatgttt aatatgctga gtacggtctt         1280
aggagtctca atcttaaatc ttgggcagaa gaggtacacc         1320
aaaaccacat actggtggga tgggctccaa tcctctgatg         1360
atttcgctct catagtgaat gcaccaaatc atgagggaat         1400
acaagcagga gtggatagat ctataggac ttgcaagcta          1440
gttggaatca acatgagcaa aaagaagtct tacataaatc         1480
ggacaggaac atttgagttc acaagctttt tctaccgcta         1520
tgggtttgta gccaacttca gcatggagct gcccagcttt         1560
ggagtttccg gaattaatga atcggctgac atgagcattg         1600
gagttacagt gataaagaat aatatgataa acaatgacct         1640
tggaccagca acagcccaga tggctcttca gctgttcatt         1680
aaagactaca gatacaccta ccgatgccac agaggtgata         1720
cacaaattca aactagaaga tcatttgaat tgaagaagct         1760
gtgggggcag acccgctcaa aggcaggact gttggtttca         1800
gatggagggc cgaatttata caacgtccga aatcttcaca         1840
ttcctgaagt ttgcttgaag tgggagttga tggatgaaga         1880
ttaccaggga agactgtgta accctctgaa cccgtttgtc         1920
agtcataagg aagttgaatc cgtcaacaat gctgtggtaa         1960
```

| | |
|---|---|
| tgccagccca tggtccggcc aagagcatgg agtatgatgc | 2000 |
| cgttacaact acacattcat ggattcccaa gagaaaccgc | 2040 |
| tccattctca acactagcca aaggggaatt cttgaggatg | 2080 |
| aacaaatgta ccagaagtgc tgcgctctat tcgagaaatt | 2120 |
| cttccctagc agttcatatc ggaggccagt tggaatttcc | 2160 |
| agcatgatgg aggccatggt gtctagggcc cgaattgatg | 2200 |
| cacggattga cttcgagtct ggaaggatta agaaagaaga | 2240 |
| atttgctgag atcatgaaga tctgttccac cattgaagtc | 2280 |
| gacatgtacc catacgatgt tccagattac gcttctagga | 2320 |
| tctgttccac cattgaagag ctcggacggc aaaaatagtg | 2360 |
| aatttagctt gtccttcatg aaaaaatgcc ttgtttctac | 2400 |
| t | 2401 |

<210> SEQ ID NO 4
<211> LENGTH: 777
<212> TYPE: PRT
<213> ORGANISM: Artificial sequence
<220> FEATURE:
<223> OTHER INFORMATION: PB1 sequence of 7attWF10

<400> SEQUENCE: 4

```
Met Asp Val Asn Pro Thr Leu Leu Phe Leu
 1               5                  10

Lys Val Pro Ala Gln Asn Ala Ile Ser Thr
            15                  20

Thr Phe Pro Tyr Thr Gly Asp Pro Pro Tyr
            25                  30

Ser His Gly Thr Gly Thr Gly Tyr Thr Met
            35                  40

Asp Thr Val Asn Arg Thr His Gln Tyr Ser
            45                  50

Glu Lys Gly Arg Trp Thr Thr Asn Thr Glu
            55                  60

Thr Gly Ala Pro Gln Leu Asn Pro Ile Asp
            65                  70

Gly Pro Leu Pro Glu Asp Asn Glu Pro Ser
            75                  80

Gly Tyr Ala Gln Thr Asp Cys Val Leu Glu
            85                  90

Ala Met Ala Phe Leu Glu Glu Ser His Pro
            95                 100

Gly Leu Phe Glu Asn Ser Cys Leu Glu Thr
           105                 110

Met Glu Val Val Gln Gln Thr Arg Val Asp
           115                 120

Lys Leu Thr Gln Gly Arg Gln Thr Tyr Asp
           125                 130

Trp Thr Leu Asn Arg Asn Glu Pro Ala Ala
           135                 140

Thr Ala Leu Ala Asn Thr Ile Glu Val Phe
           145                 150
```

```
Arg Ser Asn Gly Leu Thr Ala Asn Glu Ser
                155                 160

Gly Arg Leu Ile Asp Phe Leu Lys Asp Val
                165                 170

Met Glu Ser Met Asp Lys Glu Met Glu
                175                 180

Ile Thr Thr His Phe Gln Arg Lys Arg Arg
                185                 190

Val Arg Asp Asn Met Thr Lys Lys Met Val
                195                 200

Thr Gln Arg Thr Ile Gly Lys Lys Lys Gln
                205                 210

Lys Leu Thr Lys Lys Ser Tyr Leu Ile Arg
                215                 220

Ala Leu Thr Leu Asn Thr Met Thr Lys Asp
                225                 230

Ala Glu Arg Gly Lys Leu Lys Arg Arg Ala
                235                 240

Ile Ala Thr Pro Gly Met Glu Ile Arg Gly
                245                 250

Phe Val His Phe Val Glu Ala Leu Ala Arg
                255                 260

Ser Ile Cys Glu Lys Leu Glu Gln Ser Gly
                265                 270

Leu Pro Val Gly Gly Asn Glu Lys Lys Ala
                275                 280

Lys Leu Ala Asn Val Val Arg Lys Met Met
                285                 290

Thr Asn Ser Gln Asp Thr Glu Leu Ser Phe
                295                 300

Thr Val Thr Gly Asp Asn Thr Lys Trp Asn
                305                 310

Glu Asn Gln Asn Pro Arg Ile Phe Leu Ala
                315                 320

Met Ile Thr Tyr Ile Thr Arg Asn Gln Pro
                325                 330

Glu Trp Phe Arg Asn Val Leu Ser Ile Ala
                335                 340

Pro Ile Met Phe Ser Asn Lys Met Ala Arg
                345                 350

Leu Gly Lys Gly Tyr Met Phe Glu Ser Lys
                355                 360

Ser Met Lys Leu Arg Thr Gln Ile Pro Ala
                365                 370

Glu Met Leu Ala Asn Ile Asp Leu Lys Tyr
                375                 380

Phe Asn Glu Ser Thr Arg Lys Lys Ile Glu
                385                 390

Glu Ile Arg Pro Leu Leu Ile Glu Gly Thr
                395                 400

Ala Ser Leu Ser Pro Gly Met Met Met Gly
                405                 410

Met Phe Asn Met Leu Ser Thr Val Leu Gly
                415                 420
```

```
Val Ser Ile Leu Asn Leu Gly Gln Lys Arg
            425                 430

Tyr Thr Lys Thr Thr Tyr Trp Trp Asp Gly
            435                 440

Leu Gln Ser Ser Asp Asp Phe Ala Leu Ile
            445                 450

Val Asn Ala Pro Asn His Glu Gly Ile Gln
            455                 460

Ala Glu Val Asp Arg Phe Tyr Arg Thr Cys
            465                 470

Lys Leu Val Gly Ile Asn Met Ser Lys Lys
            475                 480

Lys Ser Tyr Ile Asn Arg Thr Gly Thr Phe
            485                 490

Glu Phe Thr Ser Phe Phe Tyr Arg Tyr Gly
            495                 500

Phe Val Ala Asn Phe Ser Met Glu Leu Pro
            505                 510

Ser Phe Gly Val Ser Gly Ile Asn Glu Ser
            515                 520

Ala Asp Met Ser Ile Gly Val Thr Val Ile
            525                 530

Lys Asn Asn Met Ile Asn Asn Asp Leu Gly
            535                 540

Pro Ala Thr Ala Gln Met Ala Leu Gln Leu
            545                 550

Phe Ile Lys Asp Tyr Arg Tyr Thr Tyr Arg
            555                 560

Cys His Arg Gly Asp Thr Gln Ile Gln Thr
            565                 570

Arg Arg Ser Phe Glu Leu Lys Lys Leu Trp
            575                 580

Gly Gln Thr Arg Ser Lys Ala Gly Leu Leu
            585                 590

Val Ser Asp Gly Gly Pro Asn Leu Tyr Asn
            595                 600

Val Arg Asn Leu His Ile Pro Glu Val Cys
            605                 610

Leu Lys Trp Glu Leu Met Asp Glu Asp Tyr
            615                 620

Gln Gly Arg Leu Cys Asn Pro Leu Asn Pro
            625                 630

Phe Val Ser His Lys Glu Val Glu Ser Val
            635                 640

Asn Asn Ala Val Val Met Pro Ala His Gly
            645                 650

Pro Ala Lys Ser Met Glu Tyr Asp Ala Val
            655                 660

Thr Thr Thr His Ser Trp Ile Pro Lys Arg
            665                 670

Asn Arg Ser Ile Leu Asn Thr Ser Gln Arg
            675                 680

Gly Ile Leu Glu Asp Glu Gln Met Tyr Gln
```

```
                    685                 690
Lys Cys Cys Ala Leu Phe Glu Lys Phe Phe
                        695                 700
Pro Ser Ser Ser Tyr Arg Arg Pro Val Gly
                        705                 710
Ile Ser Ser Met Met Glu Ala Met Val Ser
                        715                 720
Arg Ala Arg Ile Asp Ala Arg Ile Asp Phe
                        725                 730
Glu Ser Gly Arg Ile Lys Lys Glu Glu Phe
                        735                 740
Ala Glu Ile Met Lys Ile Cys Ser Thr Ile
                        745                 750
Glu Val Asp Met Tyr Pro Tyr Asp Val Pro
                        755                 760
Asp Tyr Ala Ser Arg Ile Cys Ser Thr Ile
                        765                 770
Glu Glu Leu Gly Arg Gln Lys
                        775

<210> SEQ ID NO 5
<211> LENGTH: 25
<212> TYPE: DNA
<213> ORGANISM: Artificial sequence
<220> FEATURE:
<223> OTHER INFORMATION: HAtag R primer sequence

<400> SEQUENCE: 5
catcgtatgg gtacatgtcg acttc                                          25

<210> SEQ ID NO 6
<211> LENGTH: 21
<212> TYPE: DNA
<213> ORGANISM: Artificial sequence
<220> FEATURE:
<223> OTHER INFORMATION: WFPB1-2147F

<400> SEQUENCE: 6
ccagttggaa tttccagcat g                                              21

<210> SEQ ID NO 7
<211> LENGTH: 33
<212> TYPE: DNA
<213> ORGANISM: Artificial sequence
<220> FEATURE:
<223> OTHER INFORMATION: Bm-PB1 2341R

<400> SEQUENCE: 7
atatcgtctc gtattagtag aaacaaggca ttt                                 33
```